(12) United States Patent
Laham et al.

(10) Patent No.: US 8,852,120 B2
(45) Date of Patent: Oct. 7, 2014

(54) DEVICES AND METHODS FOR TISSUE TRANSPLANT AND REGENERATION

(75) Inventors: Roger J. Laham, Brookline, MA (US); Joanna J. Wykrzykowska, Boston, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 1845 days.

(21) Appl. No.: 11/698,290

(22) Filed: Jan. 25, 2007

(65) Prior Publication Data

US 2007/0239066 A1    Oct. 11, 2007

Related U.S. Application Data

(63) Continuation-in-part of application No. 11/339,320, filed on Jan. 25, 2006, now Pat. No. 8,038,595.

(51) Int. Cl.
| | | |
|---|---|---|
| *A61B 10/00* | (2006.01) | |
| *A61M 5/178* | (2006.01) | |
| *A61B 17/34* | (2006.01) | |
| *A61M 25/00* | (2006.01) | |
| *A61B 10/02* | (2006.01) | |
| *A61B 17/00* | (2006.01) | |
| *A61B 18/00* | (2006.01) | |

(52) U.S. Cl.
CPC .... *A61B 17/3478* (2013.01); *A61M 2025/0042* (2013.01); *A61B 17/3468* (2013.01); *A61B 10/02* (2013.01); *A61B 2017/00323* (2013.01); *A61B 10/0266* (2013.01); *A61B 2017/00247* (2013.01); *A61B 2017/00969* (2013.01); *A61B 2018/00392* (2013.01)
USPC ........... 600/567; 600/562; 600/563; 600/564; 600/565; 600/566; 604/164.01; 604/170.02

(58) Field of Classification Search
CPC ........... A61B 2017/00243; A61B 2017/00247; A61B 2017/0057; A61B 2017/00323; A61B 2018/00392; A61B 17/3468; A61B 10/02; A61M 2025/0042
USPC .......... 600/562, 564, 565, 566, 567; 604/164.01, 164.06, 164.08, 164.11, 604/164.12, 164.13, 165.01, 170.02
See application file for complete search history.

(56) References Cited

U.S. PATENT DOCUMENTS

| | | |
|---|---|---|
| 3,342,175 A | 9/1967 | Bulloch |
| 5,006,122 A | 4/1991 | Wyatt et al. |

(Continued)

FOREIGN PATENT DOCUMENTS

| | | |
|---|---|---|
| WO | WO 98/54301 | 12/1998 |
| WO | WO 01/00859 | 1/2001 |

(Continued)

OTHER PUBLICATIONS

Borenstein et al., "Noncultured, Autologous, Skeletal Muscle Cells Can Successfully Engraft into Ovine Myocardium", www.circulationaha.org, p. 3088-3092, Jun. 2003.

*Primary Examiner* — Devin Henson
(74) *Attorney, Agent, or Firm* — McCarter & English, LLP

(57) ABSTRACT

Devices and methods for transplanting tissue for the purpose of regeneration, for treating a patient having injured myocardial tissue, and/or for improving cardiac function through cell regrowth. More specifically, the devices and methods obviate the need for cellular alteration. The devices comprise a hollow tube with a sharp distal end, a stylet that is disposed and movable within the hollow tube, and a stopping device that constrains movement of the stylet. The methods comprise removing intact tissue from a first region of a mammalian organ and implanting the tissue in a second region of the same organ.

44 Claims, 23 Drawing Sheets

(56) References Cited

U.S. PATENT DOCUMENTS

| | | | |
|---|---|---|---|
| 5,810,746 A | 9/1998 | Goldstein et al. | |
| 5,871,495 A * | 2/1999 | Mueller | 606/185 |
| 5,888,720 A | 3/1999 | Mitrani | |
| 5,976,164 A * | 11/1999 | Bencini et al. | 606/170 |
| 6,099,832 A | 8/2000 | Mickle et al. | 424/93.21 |
| 6,102,926 A * | 8/2000 | Tartaglia et al. | 606/170 |
| 6,110,459 A | 8/2000 | Mickle et al. | 424/93.21 |
| 6,322,548 B1 * | 11/2001 | Payne et al. | 604/500 |
| 6,432,712 B1 | 8/2002 | Wolfinbarger, Jr. | 435/395 |
| 6,485,436 B1 * | 11/2002 | Truckai et al. | 600/564 |
| 6,511,471 B2 * | 1/2003 | Rosenman et al. | 604/528 |
| 6,638,233 B2 * | 10/2003 | Corvi et al. | 600/564 |
| 6,758,848 B2 * | 7/2004 | Burbank et al. | 606/45 |
| 6,893,421 B1 * | 5/2005 | Larson et al. | 604/164.01 |
| 6,918,890 B2 * | 7/2005 | Schmidt | 604/164.01 |
| 7,067,121 B2 | 6/2006 | Mickle et al. | 424/93.21 |
| 7,097,833 B2 | 8/2006 | Freyman | 424/93.7 |
| 7,211,067 B2 * | 5/2007 | Hawk et al | 604/164.01 |
| 7,297,540 B2 | 11/2007 | Mitrani | |
| 7,309,328 B2 * | 12/2007 | Kaplan et al. | 604/264 |
| 2002/0183740 A1 | 12/2002 | Edwards et al. | |
| 2003/0086914 A1 | 5/2003 | Mitrani | |
| 2004/0039338 A1 * | 2/2004 | Lee et al. | 604/164.12 |
| 2004/0097973 A1 | 5/2004 | Loshakove et al. | |
| 2005/0288618 A1 | 12/2005 | Jenson et al. | |
| 2006/0167418 A1 * | 7/2006 | Khayal et al. | 604/164.11 |
| 2006/0189891 A1 * | 8/2006 | Waxman et al. | 600/564 |
| 2006/0263338 A1 | 11/2006 | Jacoby et al. | 424/93.7 |
| 2006/0276685 A1 | 12/2006 | Dinsmore | 600/37 |
| 2007/0059288 A1 | 3/2007 | Dinsmore et al. | 424/93.2 |

FOREIGN PATENT DOCUMENTS

| | | |
|---|---|---|
| WO | WO 02/28470 | 4/2002 |
| WO | WO 03/060062 | 7/2003 |
| WO | WO 03/061455 | 7/2003 |
| WO | WO 2004/009132 | 1/2004 |
| WO | WO 2005/112817 | 12/2005 |
| WO | WO 2006/005342 | 1/2006 |

* cited by examiner

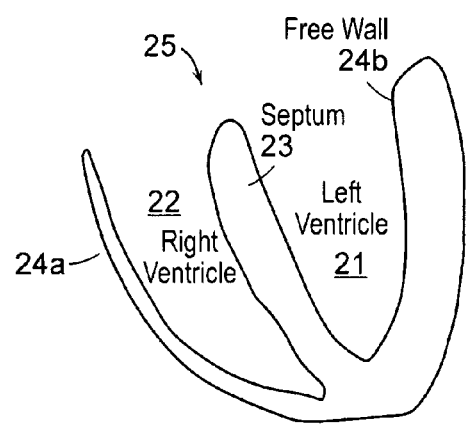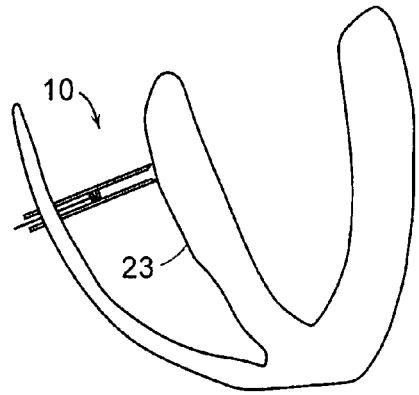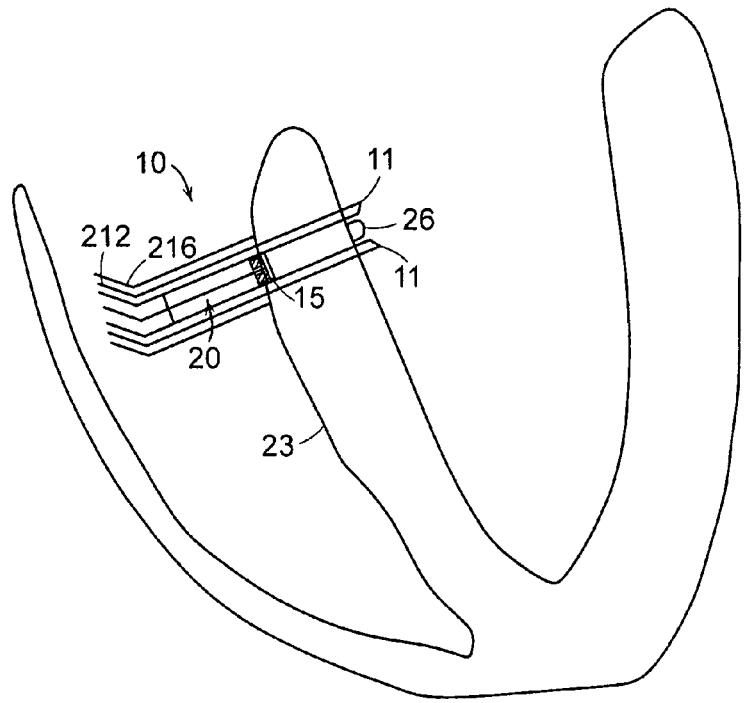

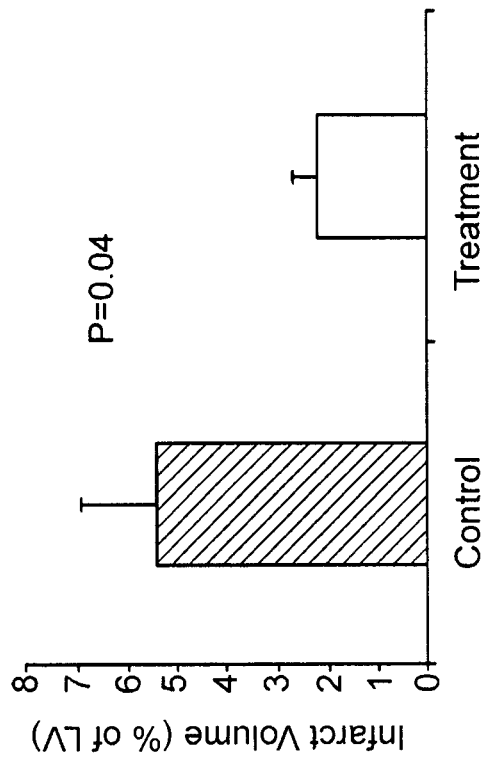
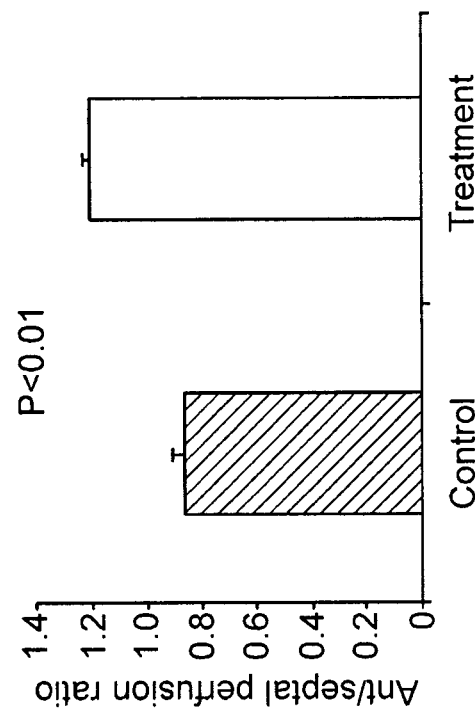
FIG. 5A
FIG. 5B

DEVICES AND METHODS FOR TISSUE TRANSPLANT AND REGENERATION

CROSS REFERENCE TO RELATED APPLICATIONS

This is a continuation-in-part application of U.S. application Ser. No. 11/339,320, filed Jan. 25, 2006 now U.S. Pat. No. 8,038,595, the entire contents of which is incorporated herein by reference.

BACKGROUND OF THE INVENTION

Myocardial infarction and ischemic heart disease in adult humans can result in dysfunction and irreversible cardiomyocyte loss, which damage and weaken the heart muscle. Cardiomyocyte loss and heart damage, if untreated, can lead to congestive heart failure, a leading cause of mortality, within a few years of the myocardial infarction or ischemia.

Myocardial functionality, especially among aging adult humans, typically, cannot be restored using a body's inherent healing mechanisms. Myocardial regeneration of cardiomyocytes in adult humans is also very limited. Furthermore, myocardial transplantation is restricted by a shortage of organ donors. Accordingly, means and methods of myogenesis and/or myocardial regeneration to supplement the adult human body's natural healing capability have become the subject of intensive research and investigation.

Cell transplantation, e.g., cellular cardiomyoplasty, is a method of replacing cardiomyocytes lost due to myocardial infarction or ischemia. Succinctly, autologous cells from other parts of the body or exogenous cells can be transplanted or engrafted in the myocardium. The transplanted or engrafted cells differentiate and, for reasons that are not fully known at this time, provide functional improvement of the myocardium.

A myriad of different cell types have been used for such cellular, or cell-based, therapies. For example, cell-based therapies have included, without limitation, adult cultured cardiac and skeletal muscle myocytes or myoblasts, progenitor cells from autologous bone marrow and/or peripheral blood, cultured mesenchymal and/or embryonic stem cells.

To enhance, cell-growth, extracted cells regardless of their source of origin can be artificially cultured. Cell culturing involves harvesting autologous muscle cells or tissue, blood cells, stem cells, culturing the cells or tissue in vitro or in vivo to provide a higher cell density and introducing the cultured cells in the damaged portion of the myocardium. Historic problems with cell culturing include the expense, the potentially hazardous nature of the harvesting process, the time needed to culture the cells, and the equipment needed to harvest and implant the cells.

Methods for improving myocardial functionality include retrieving myocyte micro-granules from a donor area placing the myocyte micro-granules in a fluid container and implanting the myocyte micro-granule fluid.

There is a continuing need for improvement in systems and methods for cellular regeneration of tissue.

SUMMARY OF THE INVENTION

The present invention discloses devices and methods for transplanting tissue from a first region of a mammalian internal organ, e.g., the myocardium, brain, liver, kidney, or bladder to a second region of the mammalian internal organ. Preferably, the method comprises removing a tissue sample from the first region of the mammalian organ and implanting the tissue sample in the second region of the mammalian organ to increase cellular growth in the second region. In this embodiment, it is preferable that the removal and implantation steps do not include an intermediate step of cellular alteration. By preserving the tissue architecture during tissue removal and implantation, the process can increase the number of resident stem cells.

In one aspect of the embodied method, when the mammalian organ is the myocardium, the method further includes removing the tissue sample from intact myocardial tissue and, more specifically, from the ventricle septum of the heart. The volume of tissue removed for cardiomyoplasty is selected so as to minimize damage to healthy tissue that will quickly heal, and at the same time provide a population of cardiac stem cells that preserves or improves cardiac function in the damaged region.

In another aspect of the embodied method, the myocardial biopsy tissue is implanted into ischemic myocardial tissue and/or a myocardial infarction (MI) region. It is preferable to perform the procedure as soon as possible after the damage to the tissue has occurred. However, the procedure is advantageous even if performed well after the initial injury.

In another embodiment, the present invention provides a method of treating a mammalian subject having injured myocardial tissue. Preferably, the method comprises removing a tissue sample from a first region of mammalian myocardial tissue and implanting the tissue sample in a second region of injured mammalian myocardial tissue to enhance cellular growth. Depending upon the size of the injured region, the surgeon can optionally perform additional tissue removal and implants at different locations to increase the rate of cellular regeneration. Thus, 2-10 or more implants can be performed for a given patient.

In still another embodiment, the present invention provides a method of improving cardiac function in a mammalian subject having an injured myocardium. Preferably, the method comprises removing a tissue sample from a first region of a mammalian myocardium and implanting the tissue sample in a second region of the mammalian myocardium to improve cardiac function by cellular regrowth. This can include, for example, improved ejection fraction and contractility of the heart.

A preferred embodiment of the invention provides a device for repairing an injured myocardium by cellular regrowth. In a preferred embodiment, the device comprises a sleeve or tube having a sharp distal end for insertion into myocardial tissue, a movable element such as a stylet that can be moved consistently within the tube to move a tissue sample within the tube and a stopping device positioned within the tube that constrains movement of the stylet. The embodied device is further suitable for retrieving a tissue sample from a donor area for implantation in a portion of a myocardium without cellular alteration of the sample and/or for transplanting tissue from a first region of a mammalian organ to a second region of the mammalian organ. The device can be employed during an open chest or minimally invasive procedure to remove and implant myocardial tissue or can be used with a percutaneous catheter system to remove and implant tissue. The device removes a volume of tissue in a range of 2 to 50 $mm^3$. The sample is preferably small enough that blood will readily move through the sample at a rate that will avoid necrosis.

The thickness of the septum determines the length of the biopsy taken which in humans ranges between 10 and 13 mm. The length of the sampling tube can vary between 5 mm and 15 mm depending upon the application. Thus the technique takes advantage of the septal anatomy to make the tissue volume and dimensions uniform. This also allows for the biopsy device to act as a cutting device without the need for tissue shearing and damage. The tube is about 100-1000 μm, preferably 200-800 μm in inner diameter. This determines the thickness of the sample which falls within the range of diffusion of blood and therefore does not require the implants to be transplanted with their own blood supply.

In another preferred embodiment of the invention, all or a portion of the removed tissue undergoes a further diagnostic or therapeutic treatment. The catheter delivery system and the myotissue implant process can also include septal biopsies that are subjected to digestion with urea which empties the extracellular matrix scaffold of its cellular elements. The matrix scaffold thus engineered can be subsequently repopulated with other cellular elements. Different cell types within the scaffold can thus be implanted within the myocardium and their potential to regenerate the myocardium and promote angiogenesis can be assessed. These cell types can include endothelial cell progenitors, smooth muscle cell progenitors or cardiomyocyte progenitors. In addition cord blood derived stem cells can also be used with this method.

Thus, the present invention utilizes a tissue scaffold or extracellular supporting tissue structure that supports a sufficient population of cells to enhance cellular regeneration of the organ. By using the selected volume of tissue, the extracellular in lieu of the sample, can be used to further improve the regeneration properties of the implant.

In addition, the scaffold with or without the cellular elements can be infused with angiogenic proteins (VEGF, FGF-2, HIF-1 and PR39) and other growth factors and thereby form a platform into which cardiac resident stem cells can migrate and in which they can find a trophic environment to grow and differentiate into mature cardiomyocytes.

Genetically engineered cells can also be implanted using this scaffold vehicle and the catheter system described herein. For instance VEGF, PI3 Kinase or Akt transfected cardiomyocytes or endothelial progenitors can be implanted. These growth factors and signaling proteins have been shown to enhance cell survival and decrease apoptosis.

This method is useful for evaluating and using individual angiogenic factors and myogenic cells and their respective regenerative properties. The scaffold allows for more sustained release of these factors rather than short-term increase in levels seen with currently available direct intramyocardial injection methods of naked cDNA.

A preferred embodiment of the invention employs a method of removing a sample in which that portion of the organ being removed has a thickness that is selected to provide a sample of a desired length. For example, in an embodiment in which it is desirable to implant a sample having a length of 5 mm, a portion of the septal wall having a thickness of 5 mm is selected for removal. This avoids the difficulty of having to cut or tear off the end of the sample from the surrounding tissue. Another embodiment involves sampling a portion of the brain in which the sampling device is inserted through the region to be sampled such that the distal end extends into a $3^{rd}$ ventricle or other cavity.

Regeneration of brain tissue can be performed in an analogous fashion to the cardiac muscle, as the brain also has limited regenerative capability. Patients affected with stroke often suffer irreversible neuron loss in the territory of one artery such as middle cerebral artery. The administration of thrombolytics to recanalyze the cerebral artery is even more time sensitive than recanalization of coronary artery during myocardial infarction as neurons are more sensitive to hypoxia. If neuronal resident stem cells are present within the brain tissue, a similar method can be applied whereby brain tissue from frontal lobes or other regions of the brain with redundant function can be implanted into the critical executive function areas of the brain that were damaged by infarction. Computer-assisted endoscopy for neurosurgical procedures can be used to obtain biopsies of the frontal lobe. The site of the biopsy can be predetermined with stereotactic mapping prior to the biopsy procedure to ensure that vital areas are not damaged. Subsequently the biopsy/implantation catheter can be inserted with the aid of the endoscope and with CT guidance to the area of brain infarction. The procedure can also be used to aid in liver regeneration with the sampling tube delivered through a laparoscopic device channel, for example.

Another preferred embodiment of the invention includes methods for measuring or monitoring the performance of the organ after implantation such as measuring perfusion, infarct volume, contractility, wall motion and ejection fraction by magnetic resonance imaging (MRI).

BRIEF DESCRIPTION OF THE DRAWINGS

The invention will be more fully understood by referring to the Detailed Description of the Invention in conjunction with the Drawings, of which:

FIG. 2A provides a diagram of a human myocardium;

FIGS. 2B and 2C provide illustrations of a method of retrieving intact myocardial tissue using a rigid device in accordance with the present invention;

FIG. 5A illustrates the ratio of anterior wall to septal wall myocardial perfusion measured by MRI.

FIG. 5B illustrates the improvement in infarct volume of treated animals measured by MRI.

DETAILED DESCRIPTION OF THE INVENTION

Figure 1A:
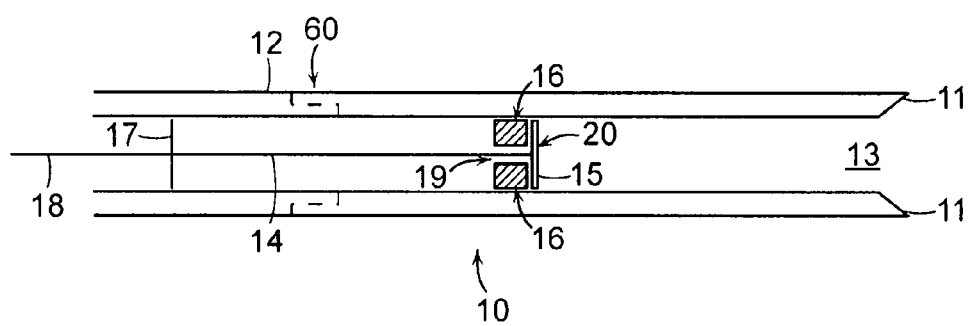
FIG. 1A provides an illustrative embodiment of a retrieval and implantation device in accordance with the present invention.

The present invention relates to devices and methods for removing a tissue sample from a mammalian organ and implanting the tissue sample into another region of the same organ or another organ of the same individual. The devices and methods can be used for cardiomyoplasty, i.e., for use with a human myocardium, and can also be used with other mammalian organs, e.g., the liver, the bladder, the kidneys and the brain. The invention is of particular significance with respect to the heart and brain in which organ or tissue transplant is not available or difficult, or where current methods of treatment are not adequate.

As previously mentioned, a variety of cells have been proposed for cellular cardiomyoplasty, e.g., adult cultured cardiac and skeletal myocytes, mesenchymal and/or embryonic stem cells, progenitors cells from autologous bone marrow and/or peripheral blood.

However, typically, cardiac stem cells implanted in an infarct zone may not form fully mature cardiomyocytes. More specifically, cardiomyocytes remained small and did not fully differentiate, producing small "islands" of cardiomyocytes.

In a first embodiment, the present invention provides a method of transplanting tissue or cells from a first region of a mammalian organ to a second region of the mammalian organ. More particularly, the method transplants intact myocardial biopsy tissue removed from the ventricle septum into a myocardial infarct region of tissue. Preferably, the method comprises removing a cell or tissue sample, i.e., intact myocardial biopsy tissue, from a first region of the mammalian organ, e.g., the myocardial or ventricle septum, and implanting the cell or tissue sample in a second region of the mammalian organ, i.e., the myocardial infarct scar or ischemic myocardial tissue. More preferably, the cell or tissue sample is implanted without an intermediate step involving cellular alteration.

Another aspect of the invention is a tissue transplantation catheter device. The body of the tissue transplantation catheter device is a hollow hypotube, preferably made of stainless steel, nitinol, or a suitable polymer material, with an internal diameter of 100-800 micrometers and an outer diameter of 1.5 mm or less. The tube is rigid down its longitudinal axis, having a fixed length. In certain embodiments, the tube is inflexible or rigid. In other embodiments, the sleeve or tube is flexible or can be oriented in all directions perpendicular to the longitudinal axis, allowing it to navigate various body lumens, such as the arterial system or the chambers of the heart. The tube has a sharp cutting edge at the distal end. Optionally, an obturator can be added during tissue insertion prior to retrieval, so as to prevent the distal end of the device from filling with tissue prior to reaching the desired donor area. A stylet is fitted into the tube and is mounted such that it is capable of retracting within the distal tip of the tube for a distance corresponding to the length of the tissue graft or biopsy. A stop is mounted within the tube so as to limit the range of motion of the stylet. For example, the stop can partially close the lumen of the tube, causing a collar at the base of the stylet to come to rest on the stop as the stylet is retracted when loading the transplantation catheter with a tissue graft. The proximal end of the hypotube is mounted onto a control handle that is fitted with various actuators for controlling the movements of the components at the distal end of the catheter. For example, in different embodiments the control handle may be fitted with one or more actuators for extending and retracting the tube, extending and retracting the stylet within the tube, regulating the length of travel of the stylet or the position of the stylet stop within the tube, and controlling the bending motion of a flexible distal end of the tube.

In one embodiment, the catheter includes a mechanism to change the effective stylet length, e.g., by moving the stop position within the tube or by changing the distance between the stylet tip and the stylet collar. By adjusting the length of the stylet, the size (i.e., the length) of the tissue graft can be set to an appropriate length. For example, in one embodiment the stylet is set to a length that equals or exceeds the thickness of tissue in the donor area, thereby preventing the tissue from tearing away when the graft is removed.

Another embodiment of the transplantation catheter device employs three stops. Each pair of stops is separated by a gap that allows the depth of the biopsy and implant to be regulated, e.g., by alternating among different actuator positions on the control handle at the proximal end of the device. The gaps can be, for example, in increments of 1 mm, 2 mm, 3 mm, 4 mm, 5 mm, or greater. By using the appropriate actuator position, a desired biopsy specimen depth can be selected during a procedure, based for example on the anatomy of the donor tissue area or the target tissue area. By way of further example, if the stops are separated by gaps of 3 mm, and the actuator selects among three settings, then a tissue graft of either 3 mm, 6 mm, or 9 mm length can be selected at the time of retrieval.

In a preferred embodiment the device allows for obtaining a myocardial tissue graft whose length corresponds to the thickness of the ventricular septum, and whose diameter corresponds to the inner diameter of the tube distal end. By harvesting a graft through the full width of the septum, the transplantation method takes advantage of septal anatomy to ensure uniform tissue volume and dimensions. The transplantation catheter acts as a cutting device when harvesting the tissue graft, allowing tissue to be removed from the donor area without producing shear and tissue damage. In one embodiment, the distal end of the catheter possesses a sliding mechanism that can be operated from the proximal end, e.g., by a one click movement of the thumb, that leads to the movement of the tube relative to the stationary stylet during implantation (see FIG. 1C).

Different embodiments of the transplantation catheter are adapted to different surgical procedures. In embodiments used for open chest surgical approaches to myocardial tissue transplantation, the tube can be rigid and about 20 to 40 cm in length, and preferably about 30 cm in length. Transplantation catheters for thorascopic use can have a rigid or flexibletubular body of about 45 to 65 cm in length, preferably about 55 cm in length. In embodiments used for percutaneous applications, the catheter is flexible and optionally steerable, except at its rigid distal and proximal portions. For percutaneous access to donor or acceptor tissue areas, the tube is about 80 to 100 cm in length, and preferably about 90 cm in length. In embodiments used for transplantation of brain tissue to brain, retina, or spinal cord, the tube is rigid and about 1 to 10 cm in length. In some embodiments, the same control handle can be employed with each of various types of tubes.

In the percutaneous access mode, the transplantation catheter device is introduced into the left ventricle through a sheath and a guiding catheter from the femoral artery in a retrograde fashion via the aortic valve. The guide catheter, e.g., a hockey stick guide, allows for positioning of the transplantation catheter against the left ventricular basal septum for harvesting a tissue graft specimen, and then movement towards the treatment area using concomitant fluoroscopic, echocardiographic and/or electromagnetic guidance. The tube also is used to deliver the tissue graft by puncturing the scar area using the cutting edge at the distal tip and injecting the graft with the aid of the stylet. The stylet is kept stationary with an inner wire as the hypotube is withdrawn, leaving the graft, for example, in the left ventricular wall. In certain embodiments the transplantation catheter includes a hemostasis valve (side arm) which allows for injections of contrast media for fluoroscopic guidance.

In another embodiment, the transplantation catheter does not require a guiding catheter, but rather has an outer sheath which, in addition to protecting the sharp cutting edge of the distal tip, allows for flexing the distal rigid portion of the device (the deflectable tip) towards the walls of the transplantation target, such as an infarcted area of the left ventricle. The mechanism to allow for this flexibility can be analogous to the "pull" wire mechanism used in flexible bronchoscopes and endoscopes, or similar to the Venture catheter in interventional cardiology (Webb reference). In the Venture catheter, the distal tip can be progressively flexed to greater than 90 degrees by clockwise rotation of a thumb wheel on the external handle. This is accomplished mechanistically by a pull wire within the catheter shaft that provides tension to one side of the catheter with respect to the other.

In one aspect of the present invention, a single device, i.e., a combined bioptome and implantation device, is used both to remove and to implant the cells or tissues. Referring to FIG. 1A, there is shown an illustrative embodiment of device 10 in accordance with the invention. Preferably, the device 10 comprises a hollow tube or catheter 12, an internal stylet 20, and a stopping device 16.

Preferably, the hollow tube 12 is made of stainless steel or nitinol and includes razor-sharp cutting edges 11 around the periphery of the distal end or tip 13 of the tube 12. The hollow tube 12 can be structured and arranged as a rigid, stand alone surgical instrument or, alternatively, it can be structured and arranged as a rigid tip disposed at the distal end of a percutanous flexible shaft.

Effective sampling and implanting can be practiced with a tube 12 having an internal diameter between about 100 and about 1000 micrometers (μm), preferably between about 200 and about 800 μm. However, larger or smaller diameter tubes 12 can, of course, be used without violating the scope and spirit of this disclosure. Furthermore, a rigid surgical device 10 can be about 30 centimeters (cm) in length whereas the rigid tip disposed on a flexible shaft can be about 2 cm in length.

The stopping device or element 16, e.g., a rubber or plastic O-ring, and the like that includes a central opening 19, is disposed at a discrete distance, e.g., between about 0.5 cm and 2.0 cm, from the distal tip 13 of the tube 12. Preferably, the stopping device 16 is fixedly attached, e.g., adhesively, to or provides a tight interference fit with the inner periphery of the hollow tube 12. The stopping device 16 can arrest or limit movement of the stylet 20 during both an intake stroke and an implant stroke and controls the size or volume of the myocardial biopsy tissue taken and implanted.

The stylet 20 is positioned within the hollow portion of the tube 12 and is structured and arranged to be movable in an axial direction within the tube 12. Preferably, the stylet 20 includes a front or distal portion 15, a rear or proximal portion 17, a stroke shaft 14, and a shaft 18. More preferably, the stylet 20 is structured and arranged so that the stopping device 16 is disposed between the distal 15 and the proximal portions 17 so that the stroke shaft 14 is movable within the central opening 19.

Some embodiments of the device offer a removable distal portion 13 which has generally the same characteristics as the distal portion described above, except that it is joined to the middle and proximal portions of the tube 12 at a coupling 60. In such embodiments, the distal tip together with the stylet 20 and stop 16 can be mated to the tube 12 by feeding the stylet shaft 18 into the lumen of the tube from the distal end, and then by connecting the distal portion 13 to the tube 12 at coupling 60. Optionally, an adhesive or other mechanism can be employed to stabilize the coupling.

Figure 1B:
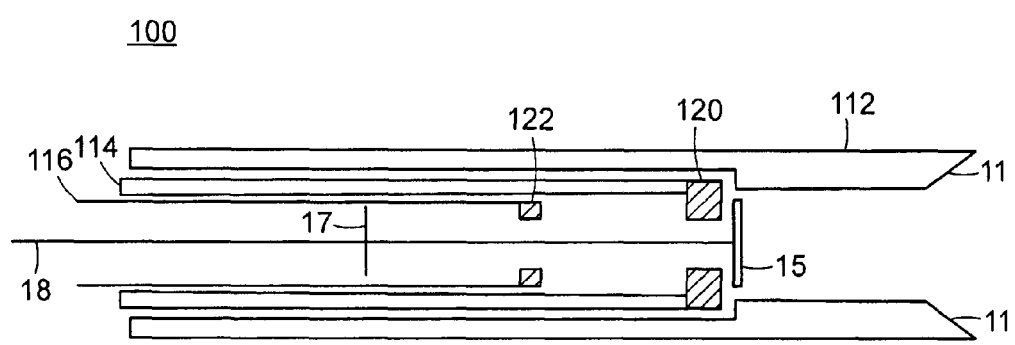
FIG. 1B provides an illustrative embodiment of a retrieval and implantation device having a movable stop affixed to a sheath.

FIG. 1B presents a variant 100 of the distal portion of the device in which two movable stops 120 and 122 are present on nested inner sheaths that can slide with respect to each other in order to adjust the length of travel of the stylet 20. By altering the position of the distal stop 120, through movement of sheath 114, the stylet position is limited upon retraction by the interaction of the distal stylet portion 15 with the distal stop 120. Similarly, by altering the position of the proximal stop 122, through movement of sheath 116, the stylet position is limited upon sample injection by interaction of the proximal stylet portion 17 with proximal stop 122.

Figure 1C:
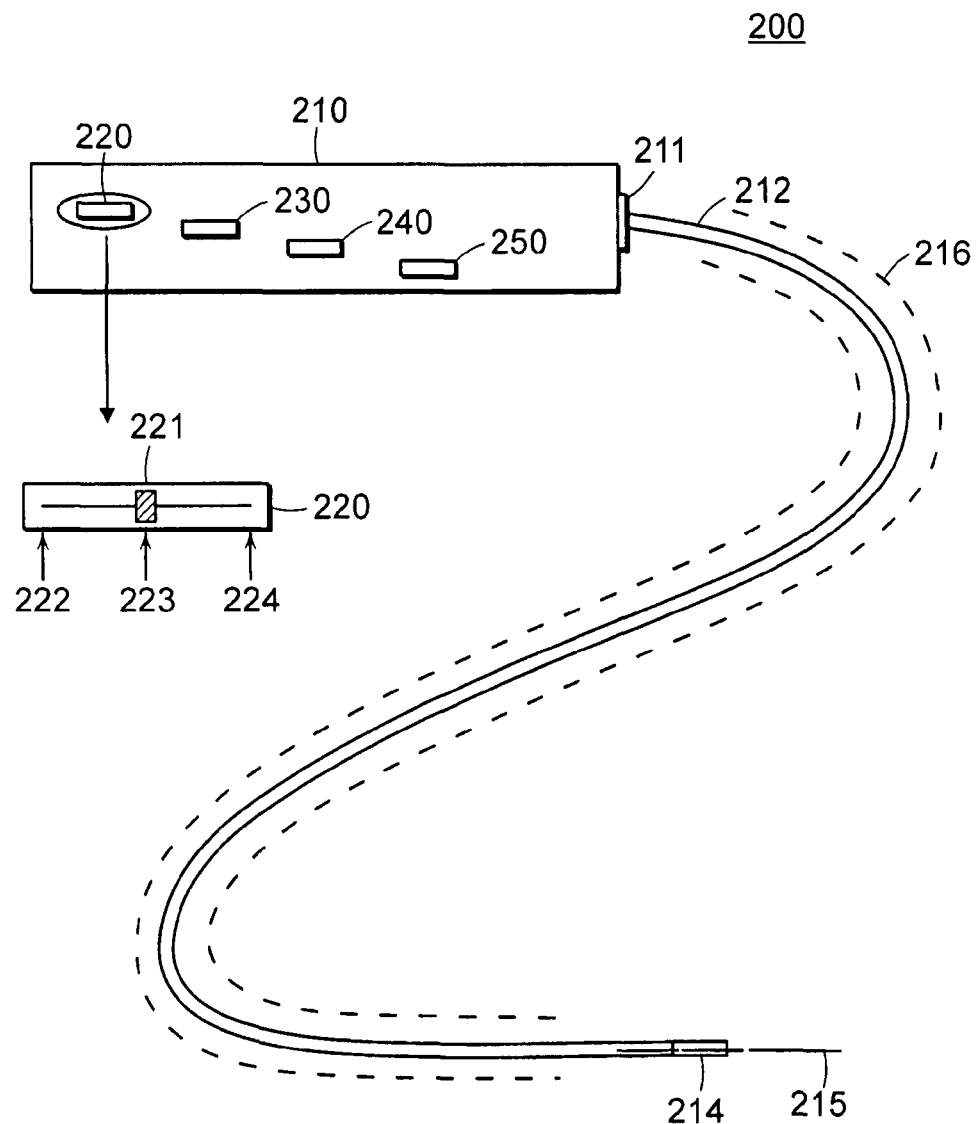
FIG. 1C provides an illustrative embodiment of a system including a retrieval and implantation device, a flexible catheter, and a control handle.

FIG. 1C illustrates an embodiment of a system 200 containing a tissue retrieval and implanting device 214 as described above coupled to a flexible hypotube 212, which in turn is connected via coupling 211 to a control handle 210. In many procedures performed with this system, the transplantation catheter device is inserted percutaneously through guide catheter 216. The control handle possesses a number of actuators that can be used to control the functions of the device. By way of example, in this embodiment the actuators 220, 230, 240, and 250 respectively control stylet retraction and extension, stylet stop position, tube extension and retraction, and anglular flexing of the distal tip portion 214. The enlarged view of actuator 220 depicts one possible control paradigm. Actuator slide 221 can be positioned within a track from full stylet extension at 224 to full stylet retraction at 222, with an intermediate position at 223, all along longitudinal axis 315. Click stops can be included in the control mechanism for convenience and reproducibility. The shape and style of the control handle and actuators are portrayed schematically. Many actual design choices are available and are well known in the art. Actuators on the control handle can be similar or dissimilar to one another in style and mechanism. Available actuator types include slides, buttons, levers, rotating knobs and the like. Note that the tube can be detachable and disposable and can also be reattached to an implant device for sample delivery.

Figure 1D:
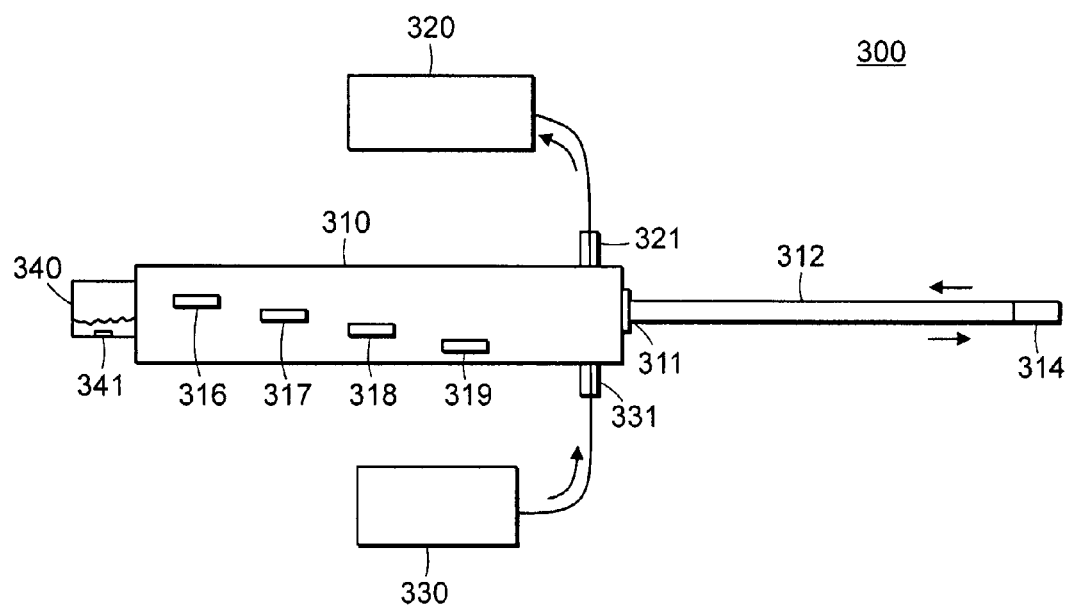
FIG. 1D provides an illustrative embodiment of a system for retrieval of a soft tissue sample by aspiration.

In FIG. 1D an embodiment of a system 300 for retrieval of a soft tissue graft specimen is illustrated. Soft tissues, such as brain, can be harvested from the donor area by an aspiration technique. The distal tip 314 is similar to embodiments already described; however, in certain variations the tip does not have a stylet or stops. The tip is joined to a rigid tube 312 having a dual lumen, which in turn is connected through coupling 311 to a control handle 310. Actuators 316, 317, 318, and 319 control the stylet extension and retraction, stylet stop position, tube extension and retraction, and anglular flexion of the distal tip portion 314. Optional additions to the control handle include a regulated vacuum supply 320 for aspiration of the tissue biopsy, coupled to one lumen of tube 312 through port 321, and a saline reservoir 330 for manual or pump-driven injection of sterile saline solution through port 331 into the second lumen of tube 312, for use in washing the tissue biopsy 341 from the collection site into a collection vessel 340. Further options include additional actuators that can be added to the handle to control the application of vacuum and saline delivery.

Figure 1E:
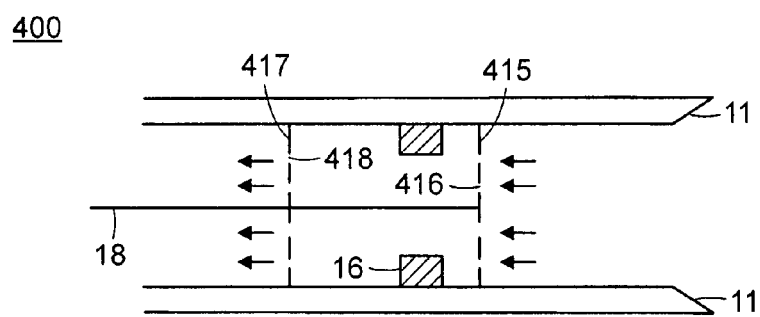
FIG. 1E provides an illustrative embodiment of a vacuum assisted retrieval and implantation device.

FIG. 1E illustrates a vacuum assisted distal tip 400. In this embodiment a gentle suction is applied to the distal stylet portion 415, through perforations 416 of the stylet surface. Similar perforations 418 are present in the proximal stylet portion 417 so as to allow continuity of pressure between the vacuum source and the tissue resting against proximal stylet portion 415. The negative pressure is used to retain the tissue graft within the distal tip between recovery and implantation. Vacuum is applied following insertion of the tip into the donor tissue and prior to withdrawal of the tip from the tissue. After the graft is in position in the donor area, the vacuum is released prior to withdrawing the hypotube to release the tissue.

Referring to FIGS. 2A to 2D, the step of removing intact myocardial biopsy tissue from the myocardial or ventricle septum using a rigid device 10, e.g., for an open chest procedure, will be described. Typically, for an open chest procedure, the device 10 is about 30 cm in length.

FIG. 2A provides a diagram of a human myocardium 25 that includes a left ventricle 21, a right ventricle 22, and a ventricle septum 23. As shown in FIGS. 2B and 2C, the device 10 is inserted through the wall 24a of the right ventricle 22, e.g., using a 3 Fr sheath or other techniques that are well known under fluoroscopic visualization in the art. The razor-sharp edges 11 of the hollow tube 12, e.g., a cutting cannula, are pressed into the septum 23. As the razor-sharp edges 11 advance further into the septum 23, the myocardial biopsy tissue 26 enters the distal end 13 of the hollow tube 12, displacing the stylet 20 by pushing against the front portion 15.

Once the front portion 15 displaces a discrete distance, e.g., about one (1) cm, from the distal end 13 of the hollow tube 12, the device 10, including the myocardial biopsy tissue 26, can be removed.

Figure 2D:
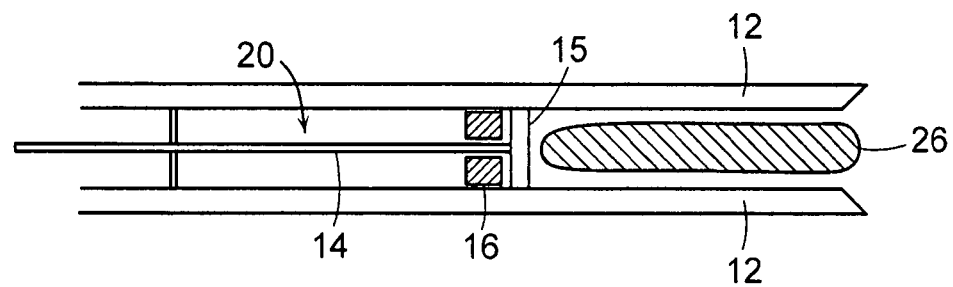
FIG. 2D provides an illustrative embodiment of a retrieval and implantation device during an intake stroke.

FIG. 2D provides an illustrative diagram of the sampling stroke of the device 10. Particularly, the stylet 20 has been pushed progressively backwards by the myocardial biopsy tissue 26 as it entered the hollow tube 12. Once the stopping device 16 and front portion 15 make contact, any further movement of the stylet 20 is arrested and the desired volume of myocardial biopsy tissue 26 is contained in the device 10.

Referring to FIGS. 3A to 3F, the step of implanting the myocardial biopsy tissue 26 in a second region of the mammalian organ using a rigid device 10 will be described. Preferably, the device 10 delivers myocardial biopsy tissue 26 to the treatment area 27 epicardially. More preferably, as previously mentioned, the embodied method obviates an intermediate, e.g., a cell culturing, step. Accordingly, myocardial biopsy tissue 26 retrieved in the first step can be implanted without cell culturing.

Figure 3A:
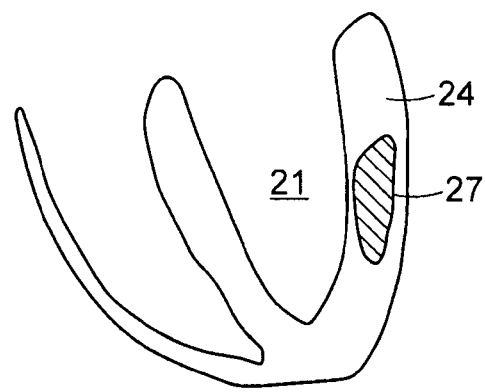
FIG. 3A provides a diagram of a human myocardium with a treatment area.
Figure 3B:
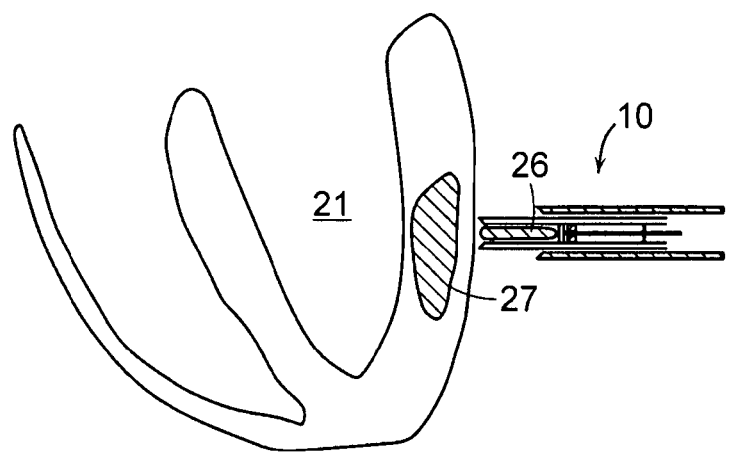
FIGS. 3B through 3D provide illustrations of a method of implanting myocardial tissue into a treatment area using a rigid device in accordance with the present invention.
Figure 3C:
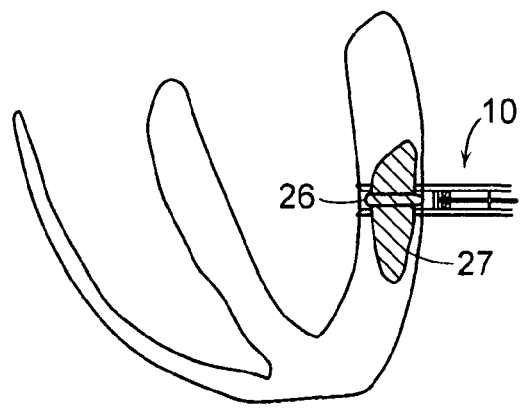
Figure 3D:
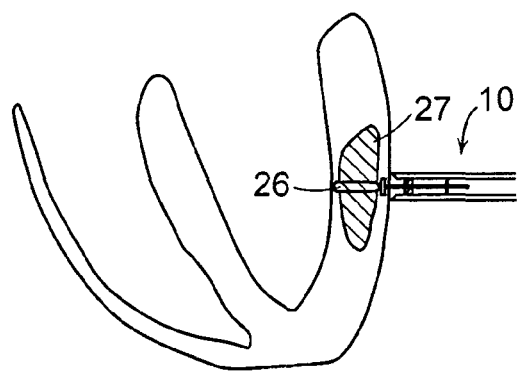

In FIG. 3A, the myocardium 25 includes a treatment area 27, e.g., a myocardial infarct scar or ischemic myocardial tissue, in the wall 24b of the left ventricle 21. As shown in FIGS. 3B-3D, after the device 10 is properly positioned with respect to the treatment area 27, the razor-sharp edges 11 of the device 10, e.g., a cutting cannula, puncture the treatment area 27; the hollow tube 12 is introduced into the treatment area 27; and the distal tip 13 of the hollow tube 12 is advanced to a discrete depth.

Once the distal tip 13 of the device 10 is positioned at the desired depth, the hollow tube 12 can be withdrawn from the treatment area. As the hollow tube 12 is being withdrawn, the shaft 18 of the stylet 20 is controlled to maintain the stylet 20 and, more particularly, the front portion 15 of the stylet 20 stationary or substantially stationary. As a result, as the hollow tube 12 is progressively withdrawn from the treatment area 27, the front portion 15 of the stylet 20 progressively extrudes the myocardial tissue sample 26, leaving the myocardial tissue 26 in the treatment area 27 of the wall 24b of the left ventricle 21.

Figure 3E:
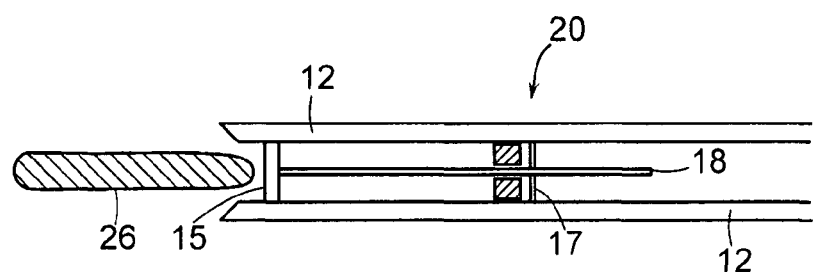
FIG. 3E provides an illustrative embodiment of a retrieval and implantation device during an implantation stroke.

FIG. 3E provides an illustrative diagram of the implant stroke of the device 10. Particularly, after insertion into the treatment area 27, the hollow tube 12 is progressively withdrawn from the treatment area 27 and the front portion 15 of the stylet 20 remains stationary or substantially stationary. As a result, the myocardial tissue 26 also is extruded into the treatment area 27. Once the stopping device 16 and rear portion 17 make contact, further movement of the stylet 20 is arrested and the desired volume of myocardial biopsy tissue 26 has been implanted in the treatment area 27.

Having described methods of taking and implanting myocardial tissue 26 using a rigid surgical device, methods of taking and implanting myocardial tissue 26 using a catheter-based system will be described. Referring to FIG. 4B, preferably, the catheter-based device 40 comprises a small, rigid tube 48 that is structured and arranged at the distal end 43 of a percutenous flexible shaft 42 that can be made using a plastic sheath or a shaped memory material such as nitinol.

In a preferred embodiment, during sampling or intake, a multi-purpose catheter or similar device can be positioned at or near the basal septum. For example, using fluoroscopic and/or echocardiographic guidance, the multi-purpose catheter can be inserted in the internal jugular vein and advanced until it is properly positioned on the basal septum. Those skilled in the art can appreciate that other points of access to the basal septum are possible and each is included herein.

Once the multi-purpose catheter is properly positioned, a tube assembly 40 comprising a percutaneous flexible shaft 42 and a rigid tube 48 structured and arranged at its distal end 43. The sharp distal edge 41 of the tube 48 is pressed into the septum to obtain intact myocardial tissue sample 46. As the sharp edge 41 advance further into the septum, the myocardial tissue 46 enters the distal end 43 of the hollow tube 48, displacing the stylet 20 by pushing against the front portion 45. Once the front portion 45 displaces a discrete distance, e.g., one (1) cm, from the distal end 43 of the rigid tube 48, the rigid tube 48, including the myocardial tissue 46, can be removed. In a preferred embodiment, a location on the septal wall is chosen where the thickness of the wall corresponds to the length of the sample being obtained. In this case, the sampling tube penetrates through the wall, thereby obviating the need to cut or tear the end of the sample from the site. Alternatively, the sampling device can include a cutting tool or edge to sever the sample from the remaining tissue.

Figure 4A:
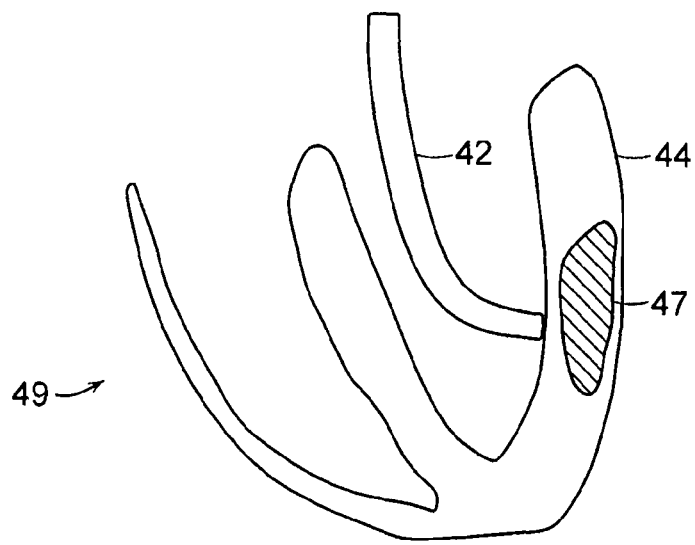
FIG. 4A provides a diagram of a human myocardium with a treatment area.
Figure 4B:
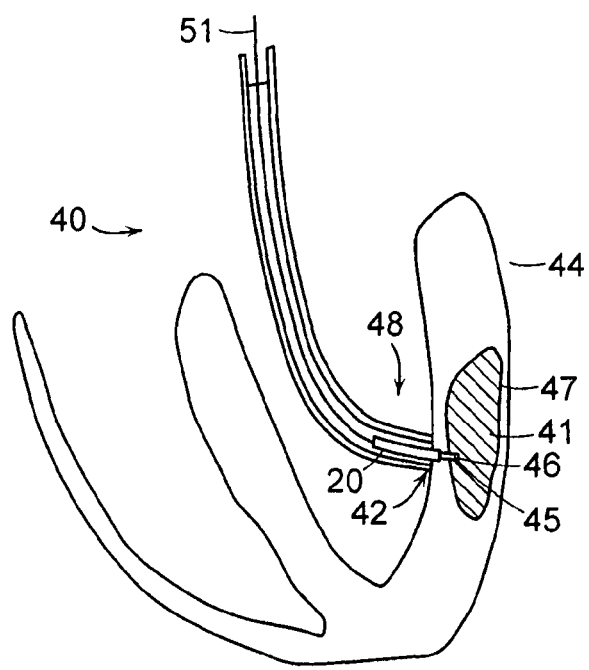
FIG. 4B provides an illustration of a method of implanting myocardial tissue into a treatment area using a catheter-based device in accordance with the present invention.

Referring to FIGS. 4A and 4B, the step of implanting the myocardial tissue 46 in a second region of the mammalian organ using a percutenous flexible shaft 42 with a rigid tube 48 will be described. Preferably, the tube assembly 40 delivers the myocardial tissue 46 to the treatment area 47, for example, a myocardial infarct scar or ischemic myocardial tissue, epicardially. As previously mentioned, the embodied method obviates an intermediate, cellular alteration, i.e., cell culturing, step.

In FIG. 4A, the myocardium 49 includes a treatment area 47 in the free wall 44. In one aspect of the present embodiment, a guiding catheter is first introduced into the myocardium 49, e.g., through the femoral artery 50, and positioned at the treatment area 47. Fluoroscopic and/or echocardiographic guidance of the guiding catheter can be used as necessary. A tube assembly 40 is then introduced into the left ventricle through a guiding catheter.

The sharp edges 41 of the rigid tube 10 puncture the treatment area 47 the hollow tube 48 is introduced into the treatment area 47 and the distal tip 43 is advanced to a discrete depth. Once the hollow tube 48 is positioned at the desired depth, the hollow tube 48 can be withdrawn from the treatment area 47.

As the hollow tube 48 is progressively withdrawn, the shaft 51 of the stylet 20 is controlled to maintain the stylet 20 and, more particularly, the front portion 45 of the stylet 20 stationary or substantially stationary. As a result, as the hollow tube 48 is progressively withdrawn, the front portion 45 of the stylet 20 progressively extrudes the myocardial biopsy tissue 46, leaving the myocardial tissue 46 in the treatment area 47 of the free wall 44 of the left ventricle.

The embodied transplantation method can also be used to increase or enhance cellular growth in a region of injured mammalian myocardial tissue and/or to improve cardiac function in a mammalian subject having an injured myocardium. Similarly, the embodied transplantation device can be used to retrieve a tissue sample from a donor area for implantation in a portion of a myocardium without cellular alteration of the sample to repair an injured myocardial region.

To measure the effectiveness of the procedure, thirteen 30-40 kg Yorkshire pigs were anesthesized with intramuscular ketamine (10 mg/kg) and isofluorane inhalation anesthesia. Right femoral artery was exposed via a surgical cutdown under sterile conditions and a 6Fr arterial sheath (Cordis, Miami, Fla.) was inserted. Heparin was administered (100 IU/kg IV). Left coronary cardiac catherization was performed and a 6Fr Hockeystick guiding catheter (Cordis) was positioned in the left main coronary artery. A 0.014" guide wire was advanced to left anterior coronary artery (LAD) and a 2.75 mm×20 mm angioplasty balloon (Maverick balloon, Guidant) was placed in the mid LAD past the take off of first diagonal branch 1 (D1) and inflated for 60 minutes to produce an anterior myocardial infarction. The location was confirmed in both right anterior oblique (30% RAO) and left anterior oblique (60% LAO) views. Ventricular fibrillation was terminated with external defibrillation and sustained ventricular ectopy was suppressed with boluses and drips of lidocaine (100 mg IV), amiodarone (75-150 mg IV) and magnesium sulfate (2-4 g IV). EKG was monitored for ST elevations. Balloon was deflated at 60 minutes and removed.

Cardiomyoplasties were performed in the acute setting of the infarction. Right anterior thoracotomy through the $4^{th}$ intercostal space was performed, the pericardium was opened and the lung retracted. Right ventricular wall was incised and a short 8Fr sheath (Cordis) was inserted, and secured with a purse string suture. A bioptome (Cook Inc, Bloomington, Ind.) was inserted via the 8Fr sheath into the RV and aimed at the septum under fluoroscopic guidance. Between 6 and 10 sample cores (average of 9) were obtained with the liver bioptome device from the right ventricular septum. In this embodiment a separate injection device is used. The samples were then transferred into a microtweezer injection device (16-gauge needle with retractable microtweezers). Seven animals were randomized to myotissue injections whereas the other 6 controls received sham injections. The animals were then allowed to recover for 4 weeks.

The animals underwent MRI on a 1.5 T General Electric TwinSpeed Scanner (GE Healthcare Technologies, Milwaukee, Wis.) 4 weeks after infarction. The following measurements were performed: 1) extent of myocardial necrosis defined as areas of myocardium showing thinning, absent wall motion and no contrast uptake on perfusion imaging, 2) resting left ventricular ejection fraction (EF), and 3) to assess myocardial perfusion using magnetic resonance first-pass perfusion analysis, and 4) myocardial infarction volume as assessed by delayed enhancement imaging.

The animals were placed in the right antecubital position, and a phased-array cardiac coil was placed around the chest. Mechanical ventilation and gaseous anesthesia was continued during scanning. Scout images were obtained to determine the short and long axis views of the heart. Using the fast imaging employing steady-state acquisition (FIESTA) pulse sequence assessed global LV function. Short axis cine images were acquired with ECG gated and without breath hold. The heart was imaged from base to apex with eight to ten LV short axis slices. The image parameters were as follows: TR/TE=3.8/1.7 ms, flip angle was 45°, 224×224 matrix, 8 mm slice thickness no gap, bandwidth 125 kHz, field of view 26 cm and 1 NEX.

MR Perfusion images were acquired in three slices each matched to short axis cine slice, representing the basal, mid-ventricular, and apical myocardial segments, with ECG gated and a non-breathhold fast gradient echo-echo train with multi phase (FGRET-MP) pulse sequence. After three to five heart beat initiation of the sequence as the baseline images, first-pass perfusion images were acquired after intravenous injection of 0.1 mmol/kg bodyweight gadolinium-DTPA (Magnevist, Berlex Laboratories, NJ) which was injected at the rate of 3.0 ml/sec, followed by a 20 ml saline flush at the rate of 3.0 ml/sec by an infusion pump, total 50 phases were acquired each slice. Imaging parameters included the following: TR/TE=9.3/1.8 ms, inversion time 160 ms, echo train length of four, 128×128 matrix, flip angle 25°, 26 cm field of view, 8 mm slice thickness, 2 mm section spacing, 125 kHz bandwidth.

Infarct size was analyzed by using the delayed-enhancement MRI technique. Images were acquired 15 min after first-pass perfusion imaging. By using an ECG-gated, non-breathhold, 2D interleaved, inversion recovery, fast-gradient recoiled echo pulse sequence. A total of 8-10 continuous short-axis slices were prescribed to cover the entire LV from base to apex. Imaging parameters were as follows: TR/TE=6.7/3.2 ms, inversion recovery time 180~220 ms, flip angle=20°, 256×192 matrix, 8 mm slice thickness/no gap, bandwidth 31.25 kHz, 26 cm field of view and 2 NEX. Inversion recovery time was adjusted as needed to null the normal myocardium.

All the measurements were analyzed offline by independent blinded investigator with commercial software (MASS Analysis, General Electric). For the myocardial perfusion analysis, short axis images were sorted according to slice position and acquisition time, the LV endocardial and epicardial contours were draw manually and six equiangular segments (anterior, antero-lateral, inferior, infero-septal, antero-septal) per slice were generated automatically, the anterior septal insertion of the right ventricle as a reference point. The upslopes of the myocardial signal in six segments were divided by the upslope of the signal in the left ventricular cavity, which was regarded as a measure of the input function.

LV pressure was measured with a high fidelity micromanometer catheter placed into the LV in a retrograde fashion. The rate of change of LV pressure was measured and averaged over 10 beats (dP/dt). All data was recorded digitally and stored for off-line analysis (Sonosoft from Sonometrics Corporation, Ontario Canada).

Four weeks after infarction and treatment, animals were sacrificed with lethal injection of pentobarbital. At the end of the experiment the hearts were harvested and cut into 5 standardized slices. The apical and the middle slice were taken for staining with 1% TTC in phosphate buffer (Sigma Chemical). The heart slices were incubated for 20 minutes at 38 degrees C. Stained slices were placed on clear acetate glass and the infarct area was measure by planimetry. Remaining cardiac muscle tissue was placed in 10% formalin in buffered saline for paraffin embedding and hematoxyline and eosin staining. Tissue was also snap frozen in liquid nitrogen at −80 degrees C. for subsequent protein analysis (for VEGF, FGF-2 TGF-beta, and PECAM-1 protein expression).

Myocardial cells were lysed by RIPA solution (Boston Bioproducts; Ashland, Mass.) and fractionated by 10% SDS-polyacrylamide gels. Protein extracts were transferred to polyvinylidene difluoride membranes (Millipore; Bedford, Mass.). VEGF, FGF-2, TGF-beta and PECAM-1 were detected with their respectively specific antibodies (Santa Cruz Biotechnology, Calif.). Immunoblots were visualized by enhanced chemiluminescence Western blotting detection reagents (Amersham Life Science; Arlington Heights, Ill.). All values of image densitometry studies were quantitated by ImageQuant software and adjusted by sample loading.

Data analysis and graphing was performed using Statview software package. Groups were compared using two-tailed student t-test with p-value cut off for statistical significance of 0.05. Normal distribution of the data was verified before performing parametric analysis. Appropriate correction was made for multiple comparisons.

The initial creation of the myocardial infarction method with balloon occlusion was associated with less than 20% mortality secondary to ventricular fibrillation during balloon occlusion. There was no additional mortality associated with the implantation procedure. The animals tolerated both the sample removal of the right ventricular septum and the anterior wall implantation without hypotension or sustained arrhythmia. The engrafted tissue remained viable as shown by subsequent histological and morphometric evaluation at 4 weeks post-implantation.

The LV myocardium was divided into six equiangular segments per slice. For each slice, perfusion in anterior wall, anteroseptal wall, and lateral wall were measured by MR first-pass perfusion based on the maximal upslope of myocardial signal intensity enhancement versus time. The ratio of perfusion in the treated anterior wall to untreated septal wall was $1.2\pm0.12$ in the treated animals versus $0.86\pm0.05$ in controls (p<0.01). Namely, perfusion was greater in the anterior wall in treated animals than in control animals but it did not differ in the septal area where no treatment was applied. The results are illustrated in FIG. 5A. Differences in perfusion as assessed by MRI correlated with global assessment of myocardial function as well as infarct volume measurements.

Mean volumes of myocardial infarct as measured by delayed enhancement on MRI were $2.2\pm1.5$ ml versus $5.42\pm0.5$ ml in the treated versus control animals (p=0.04; FIG. 5B) indicating that myotissue transplantation decreased infarction size. Measurements were made in the same slice of the myocardium that was used to assess perfusion.

Figure 6A:
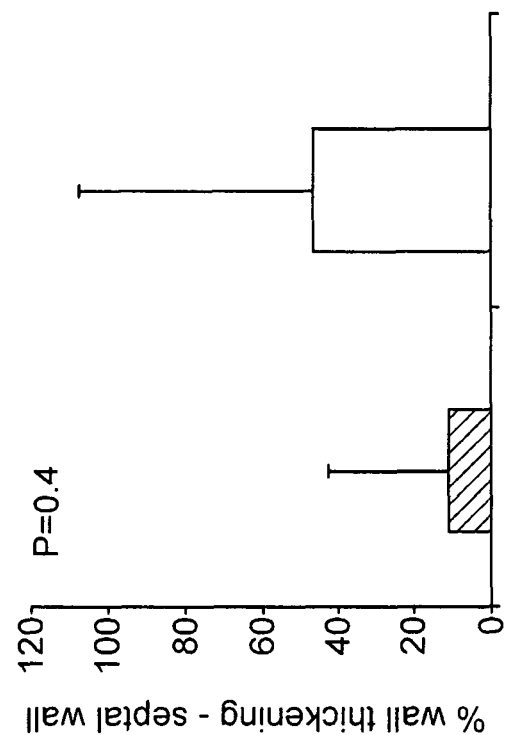
FIGS. 6A and 6B illustrate wall thickening in the anterior and septal wall, respectively, as measured by MRI.
Figure 6B:
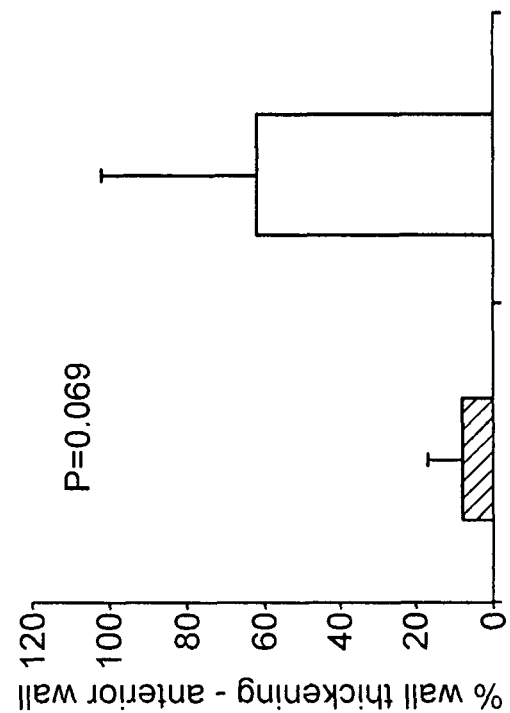
Figure 7B:
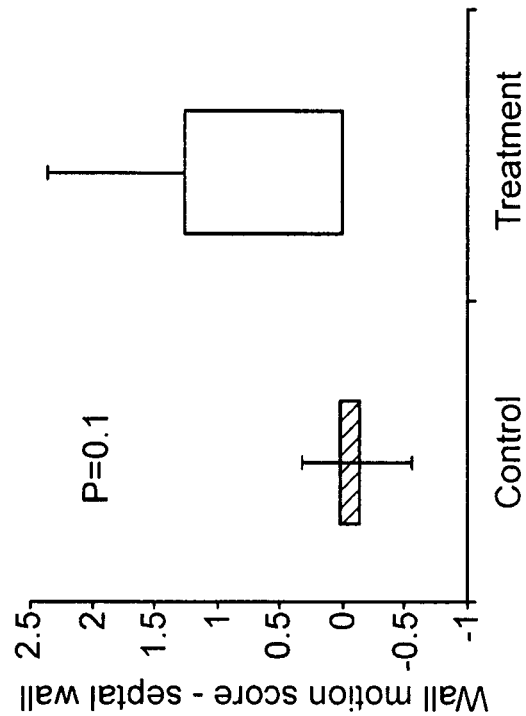
FIGS. 7A and 7b shows anterior and septal wall motion as measured by MRI.
Figure 7A:
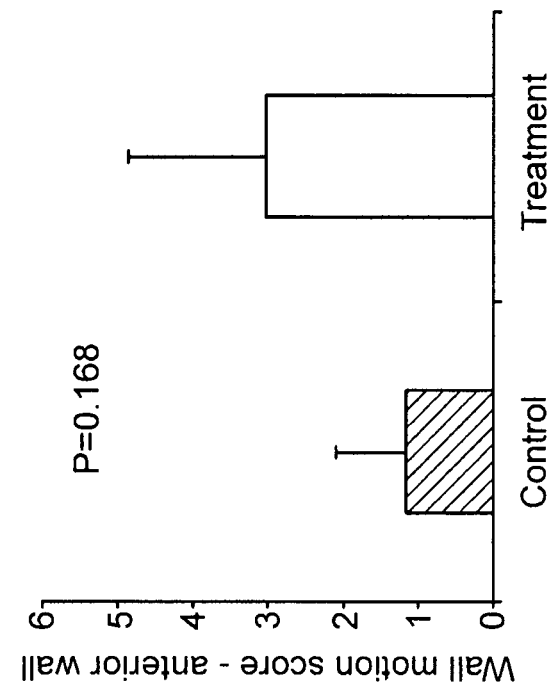
Figure 8A:
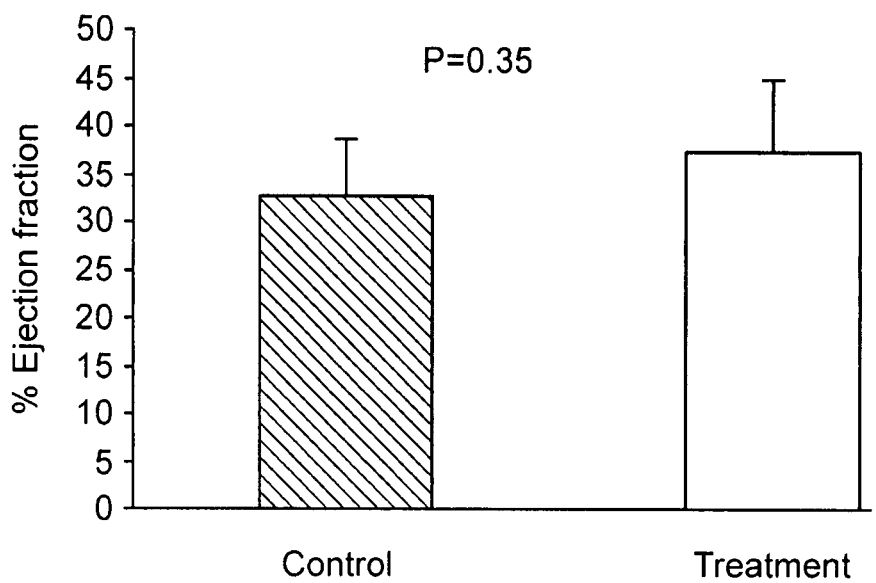
FIG. 8A illustrates the improvement in ejection fraction as measured with MRI.

Percent wall thickening was six-fold greater in the anterior wall of the treated animals than in their untreated counterparts with the result reaching statistical significance (p=0.069) (FIGS. 6A and 6B). No such difference was seen in the non-implanted septum (p=0.4). Concomitantly, the wall motion score tended to increase in the anterior wall of the implanted animals compared to the controls (p=0.17), as well as the septum likely due to translation of the improved contractility in the adjacent anterior wall (FIGS. 7A and 7B). The difference in the overall ejection fraction between the two groups (32% vs 37%; p=0.35) did not reach statistical significance (FIG. 8A).

Figure 8B:
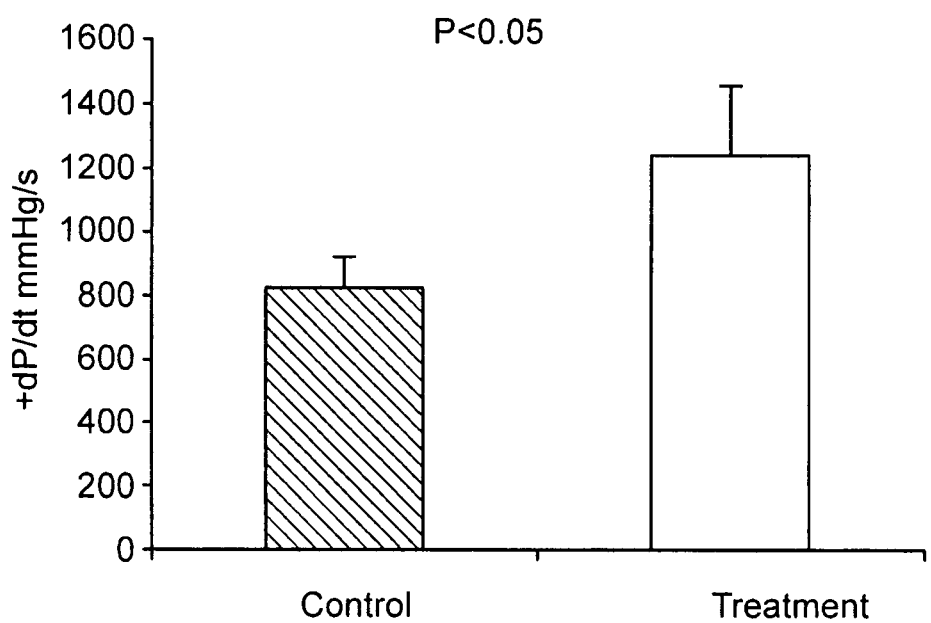
FIG. 8B illustrates the improvement in contractility in treated animals measured by micromanometer catheter.

Contractility as measured by maximal dP/dt was $1295\pm215$ mmHg/s in the treated group and $817\pm91$ mmHg/s in the control group (p<0.05) indicating that the overall systolic myocardial function improved in the treated animals (FIG. 8B) in agreement with the percent anterior wall thickening MRI results.

Figure 9B:
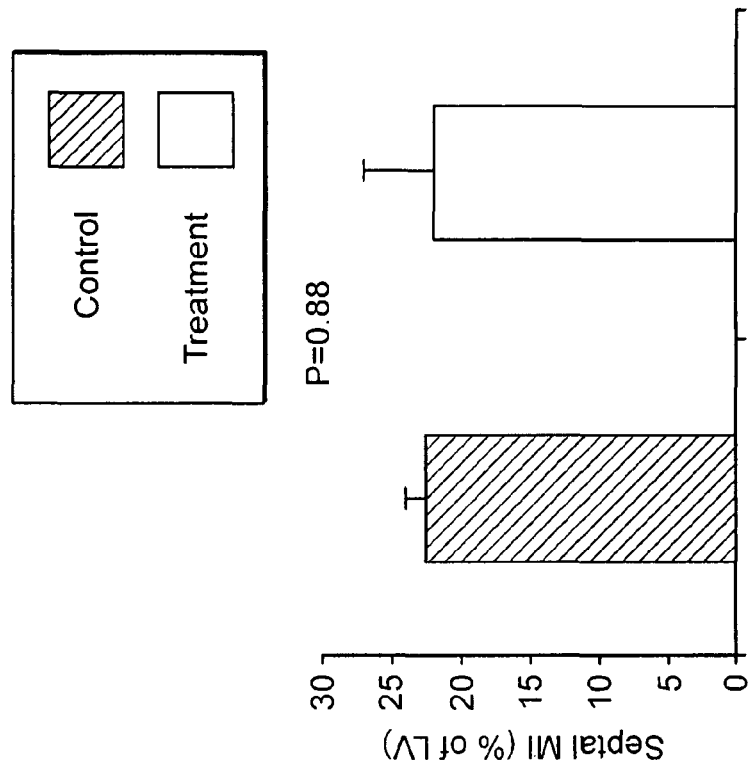
FIGS. 9A and 9B show changes in infarct size in the anterior and septal wall, respectively, as measured by TTC staining.
Figure 9A:
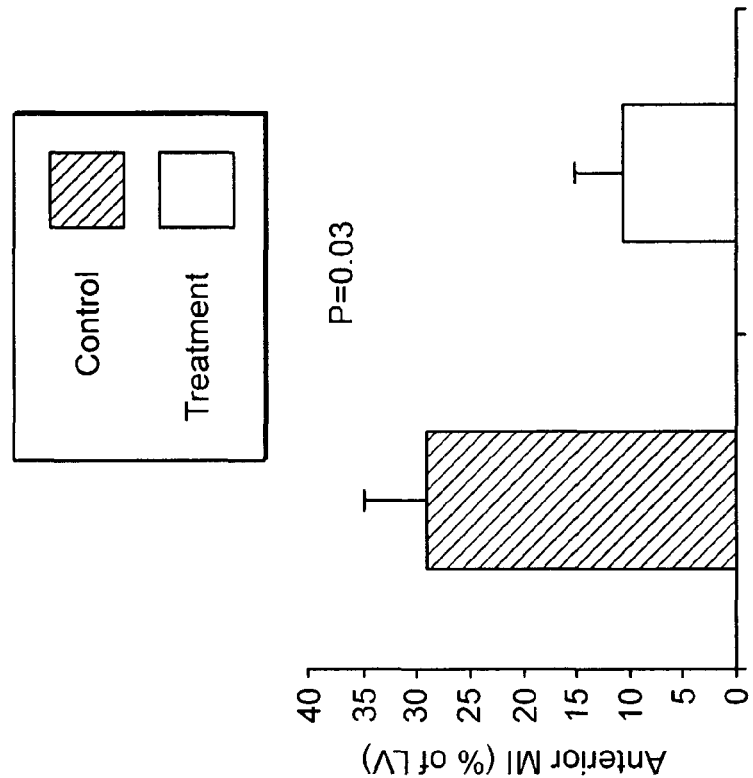
Figure 10A:
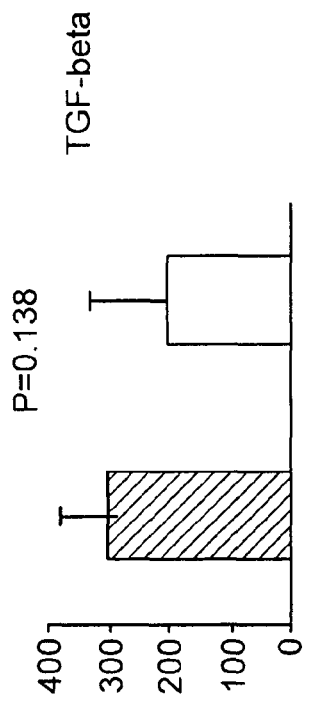
FIGS. 10A-10D shows changes in angiogenic and anti-apoptotic protein expression in untreated and treated animals.
Figure 10C:
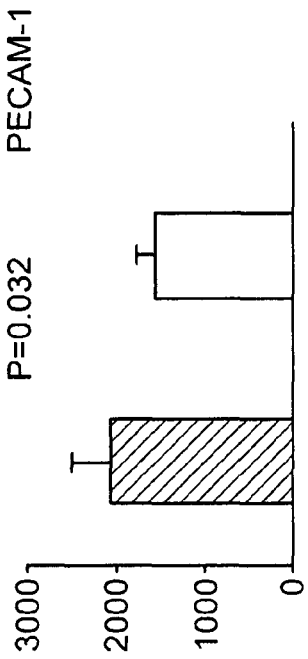
Figure 10B:
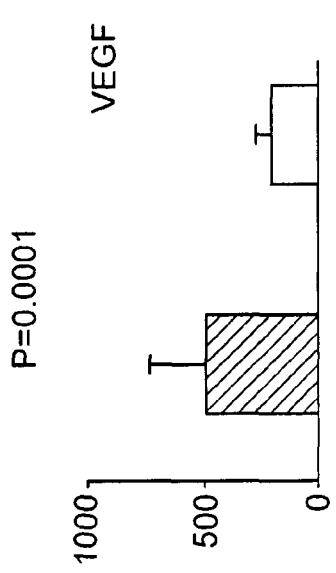
Figure 10D:
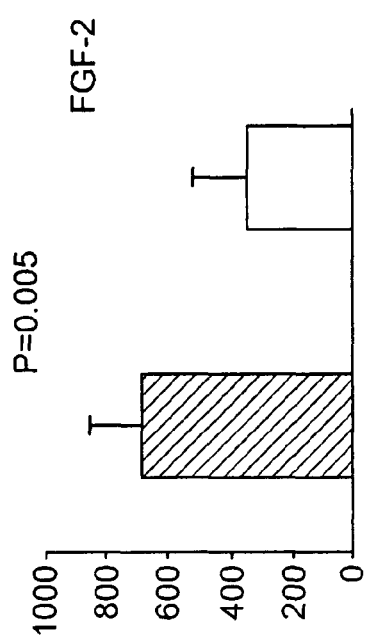

Morphometric measurement of myocardial infarction size by TTC was done to determine the effect of myotissue transplantation on infarct size. Infarct size was controlled by positioning the balloon in the mid LAD (past D1) during each procedure and maintaining inflation for 60 minutes. Despite standardizing the procedure, infarct size varied somewhat between animals due to anatomic variation. Since one can not control exactly the infarct size between the animals, the size of anterior wall infarct was normalized to the size of septal infarct, as anterior wall infarction was treated whereas the septum was not, septal infarct size served as internal control for each animal. To account for the animal to animal infarct size difference and isolate the effect of myotissue transplantation on the anterior wall we compared the percent anterior wall to septal infarct size (FIGS. 9A and 9B). There was a significant difference in infarct size between untreated and treated animals. The percent infarct size of the anterior wall area in the treated animals was $11\pm4.5$% vs $29\pm5$% in untreated animals (p=0.03). There was no difference between the two groups in percent infarct size of the septal area (21% vs 22%; p=0.88).

In order to explore the mechanisms underlying improvement in perfusion and myocardial function due to cardiomyoplasty, histopathological and protein expression analysis were performed on infarcted myocardium. Levels of VEGF, FGF-2, and PECAM-1 protein were significantly lower in treated animals. In addition, levels of TGF-beta tended to be lower in the infarcted anterior wall of treated animals compared to the non-infarcted zone. Densitometry measurements from Western blots are shown in FIGS. 10A-10D.

Described herein is a safe, effective and simple method of performing cardiomyoplasty with the entire intact autologous myocardial tissue that obviates the need for cell culture with its potential complications of infection and decreased survival of cells. This approach can be implemented with relative ease during planned revascularization procedure such as coronary artery bypass grafting (CABG).

More importantly, implantation of the whole tissue biopsy avoids cell shearing and preserves intact tissue architecture as well as the natural cytokine and growth factor milieu within the extracellular matrix scaffold. It is possible that improvement in perfusion observed locally in the anterior wall that was treated with cardiomyoplasty is due to the growth factor secretion from the extracellular matrix of the implants. Our Western blot analysis, however, showed decreased levels of angiogenic factor expression (VEGF, FGF-2) within the infarct zone as the LV function normalized. The tissue was harvested 4 weeks post-implantation. The levels, thus reflected, a completed repair process and neovascularization in the treated group. Cardiac stem cells may be contained within the biopsy tissue and may be able to differentiate into arterioles, and provide enough of a regenerative potential that the need for elaboration of high levels of angiogenic proteins by the infarct zone is partly decreased. The endothelial cells contained within the tissue sample may be capable of migrating to the epicardial coronary vessels and repairing the endothelium thereby contributing to improved perfusion and improved endothelial function.

It has been documented that stem cells and myocyte cell implantation does not result in synchronously beating new cardiomyocyte formation but rather improves myocardial function globally by positively affecting the remodeling process in the adjacent regions in addition to the implantation site. The decreased infarct volume in treated animals compared to untreated ones implies that the process of myocardial regeneration has taken place. Implantation of cardiomyocytes with extracellular matrix milieu and growth factors are better than when individual cells are injected into the unfavorable milieu of the scar. This cardiomyoplasty technique resulted in a global improvement in myocardial function as evidenced by increased peak contractility (dP/dt) on hemodynamic measurements likely deriving from decreased filling pressures and wall tension. The present MRI measurements show improvement in both perfusion and a decrease in the infarct volume within the treated anterior wall. In addition, the percent thickening of the implanted anterior wall was improved in the treated animals compared to the untreated ones, as was the wall motion score. This indicates a direct contribution of the implant to the anterior wall contractility. The improvement in contractility in the untreated adjacent septum was not statistically significant, and the slight trend to improvement in the wall motion score was likely due to the translated motion of the anterior wall. The magnitude of difference in the ejection fraction was not statistically significant, likely due to low number of animals and individual animal variability. The functional analysis results were also confirmed by morphometric analysis with TTC staining and demonstrated that infarct size was smaller in the treated anterior wall compared to the untreated septum. Histological analysis confirmed the viability of transplanted tissue at 4 weeks after implantation.

There is a comparison of the infarct volumes by MRI in the implanted and sham operated groups. The infarct size as normalized by septal infarct size was not different in the two groups. Infarct volumes were 40% lower in treated animals.

To measure the effect of the removal and implant procedure on tissue two weeks after infarction twelve Yorkshire pigs were anesthetized and a 6 Fr arterial sheath was inserted in the femoral artery for the purpose of introducing an angioplasty balloon in the left anterior coronary artery. The balloon was inflated for 60 minutes to produce an anterior myocardial infarction.

Ventricle fibrillation was terminated and external defibrillation and sustained ventricular ectopy was suppressed with boluses and drips of lidocaine, amiodarone, and magnesium sulfate. Balloons were deflated at 60 minutes and removed.

The animals were allowed to recover for two (2) weeks, after which cardiomyoplasties as described herein were performed, which is to say, that the right ventricle wall was incised and a short 8 Fr sheath was inserted. A bioptome was inserted into the right ventricle via the 8 Fr sheath, aimed at the septum.

Between six and ten samples were obtained from the right ventricle septum and the samples were implanted into the anterior wall of the left ventricle about 0.5 cm from the left anterior coronary artery and the D1/D2 bifurcation.

Two weeks after myocardial infarction and at the time of cardiomyoplasty baseline echocardiography was performed to assess for any changes in left ventricle ejection fraction and regional wall motion, and left ventricle end diastolic dimension. Recordings of two-dimensional echocardiography were performed from the left parasternal axis windows with the animal in a supine position.

End systolic (ES) and end diastolic (ED) left ventricle cavity diameters at the level of midpapillary muscles were determined in the M-mode. Ejection fraction was calculated using the equation:

$$(ED_{volume} - ES_{volume})/ED_{volume} \times 100.$$

Wall motion abnormalities were assessed in short parasternal axis views. In order to visualize the apex, which was affected by the infarct, epicardial echocardiography was also performed at the time of the thoracotomy and standard epicardial views were obtained. Measurements were repeated at four (4) weeks post-infarction at the time of organ harvest.

Left ventricle pressure was measured with a high fidelity micromanometer catheter placed into the left ventricle in a retrograde fashion. The rate of change of left ventricle pressure was measured and averaged over 10 beats (dP/dt). All data were recorded digitally and stored for off-line analysis as previously described.

Left atrial pressures were measured with a 3.5 JL 5F catheter and also recorded on Sonosoft software. These measurements were obtained at the time of the implantation two (2) weeks after the initial myocardial infarction as well as at the time of harvest at four (4) weeks after the myocardial infarction.

At the end of the experiment the hearts were harvested and cut into five (5) standardized slices. The apical and the middle slice were taken for staining with 1% triphenyl tetrazolium chloride (TTC) in phosphate buffer. The heart slices were incubated for 20 minutes at 38° C. Stained slices were placed on clear acetate glass and the infarct area was measure by planimetry. More specifically, two independent observers measured the infarct area and the results were subjected to statistical analysis.

Remaining cardiac muscle tissue was placed in 10% formalin in buffered saline for paraffin embedding and hematoxyline and eosine staining, as well as trichrome staining. Tissue was also snap frozen in liquid nitrogen at −80° C. for subsequent protein analysis, e.g., VEGF, FGF-2, PECAM and anti-apoptotic protein IAP-2 staining, and matrix metalloproteinase expression. The animals were sacrificed with lethal injection of pentobarbital.

Myocardial cells were lysed by RIP A solution and fractionated by 10% SDS-polyacrylamide gels. Protein extracts were transferred to polyvinylidene difluoride membranes. VEGF, FGF-2, IAP-20 and PECAM were detected with their respectively specific antibodies. Immunoblots were visualized by enhanced chemiluminescence Western blotting detection reagents.

All values of image densitometry studies were quantified by ImageQuant software and adjusted by the ratio of sample loading by Ponceau Red staining and normalized to the infarct size.

Paraffin tissues were subjected to the antigen retrieval techniques, i.e., immersion in boiling citrate buffer. Immunohistochemistry was performed using anti-sca-1 at 1:250 dilution, mdr-1 at 1:40 dilution, and c-kit at 1:200 dilution. Antiisotype secondary antibodies (dilution 1:250) and streptavidin-biotin system with diaminoxybenzidine development system was used to visualize the primitive stem cells. Sections were counterstained with hematoxyline and coverslipped.

Cells were counted using image analysis software, e.g., SpotAdvanced. Cells were counted in several representative 10× power fields in each animal. Data are presented as the average number of cells per 10× power field.

Data analysis and graphing were performed using the Statview software package. Groups were compared using two-tailed student t-test with p-value cut-off for statistical significance of 0.05. Normal distribution of the data was verified before performing parametric analysis. Appropriate correction was made for multiple comparisons. Data are expressed as means with standard deviations with the exception of TTC staining data where standard error was used given that two separate measurements were made per animal and treated as individual samples. Similar analysis was performed in an acute model of myocardial infarction.

The initial creation of the myocardial infarction with balloon occlusion was associated with 20-30% mortality secondary to ventricular fibrillation during the balloon occlusion. There was no additional mortality associated with the cardiomyoplasty procedure. The animals tolerated both the biopsy of the right ventricle septum and the anterior wall implantation well without hypotension or arrhythmia. The engraftment was approaching 100% as shown by subsequent histological and morphometric evaluation at four (4) weeks post-implantation.

Figure 11A:
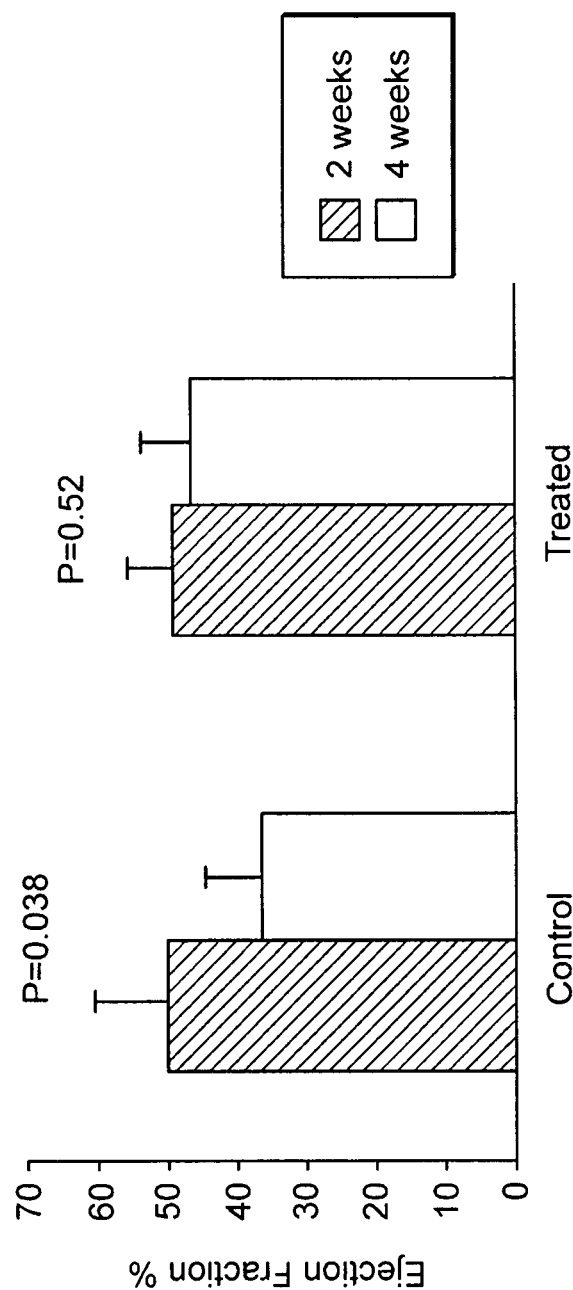
FIG. 11A illustrates the prevention of deterioration in ejection fraction in treated subjects at two and four following myocardial infarction.

Animals treated with myotissue maintained the same ejection fraction at two (2) and four (4) weeks post-infarction (49%±6.5% vs. 46%±7.4%; p=0.52). In contrast, as shown in FIG. 11A, ejection fraction decreased significantly in untreated animals (50%±10.4% vs. 36%±8.7%; p=0.038). This indicated that myotissue implantation prevented unfavorable changes that ensue after myocardial infarction.

Figure 11C:
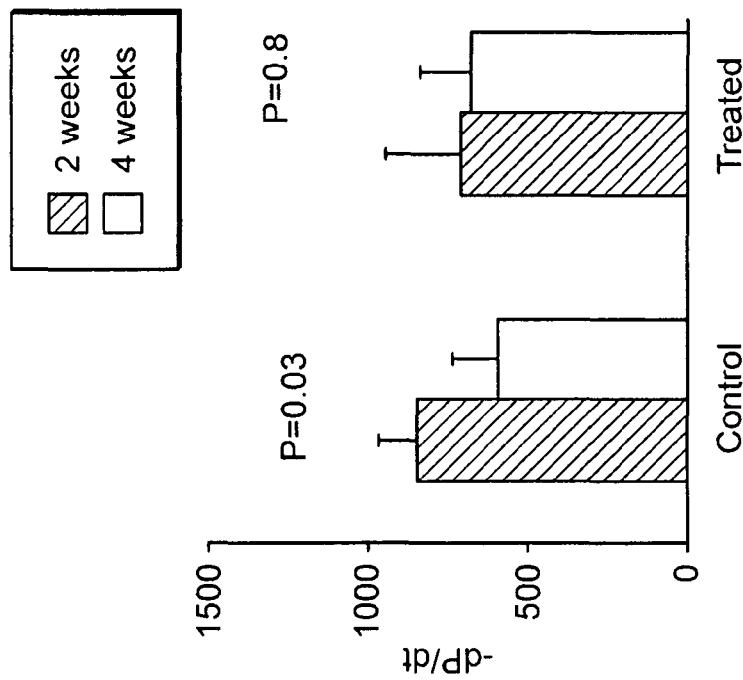
FIGS. 11B and 11C show the hemadynamic assessment of contractility and relaxation, respectively.
Figure 11B:
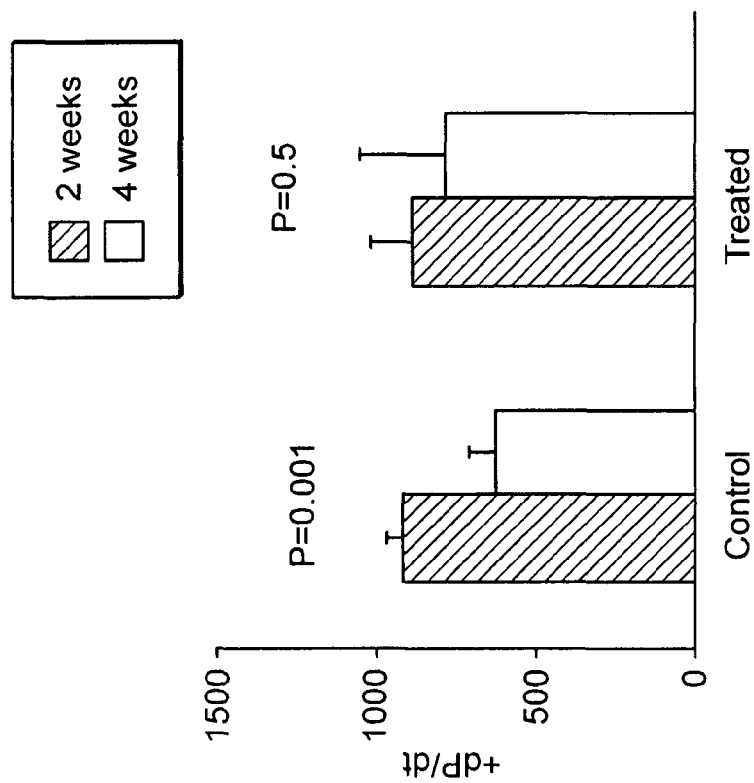
Figure 11D:
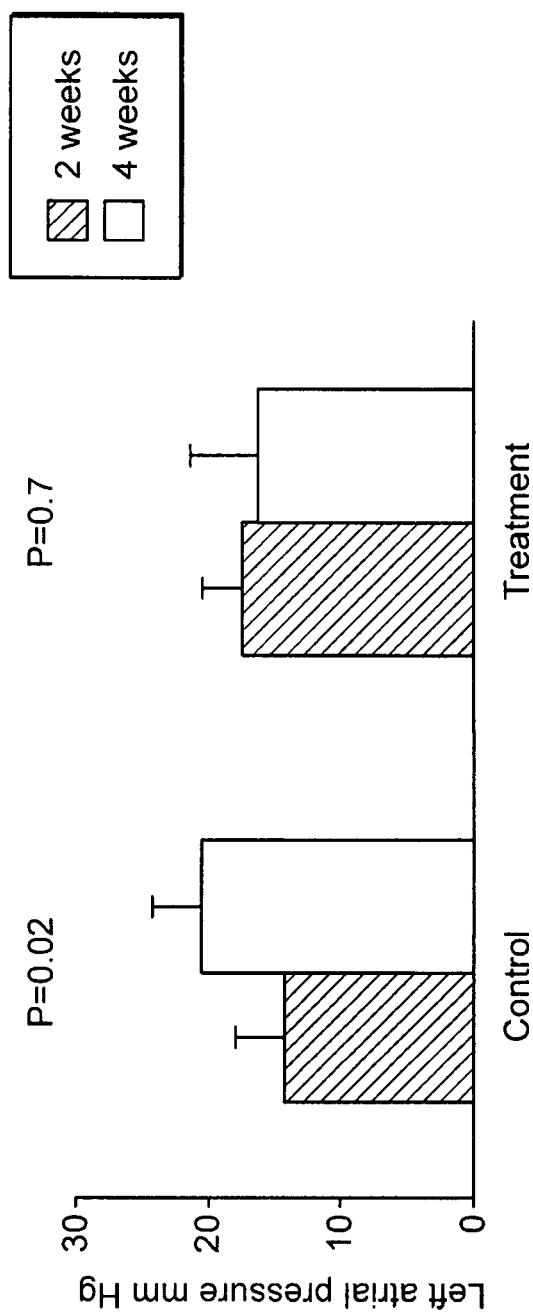
FIG. 11D shows the left atrial pressure remains normal in treated subjects and is elevated at four weeks in untreated subjects.

Hemodynamic assessment results paralleled the echo results in that both systolic (positive dP/dt) and diastolic (negative dP/dt) function, as well as filling pressures did not change in the treated animals between weeks two (2) and four (4) post-infarction (FIGS. 11B, 11C and 11D, respectively). The left atrial pressures were 17 versus 16 (p=NS), dP/dt was 874 versus 763 (p=NS) and negative dP/dt was 716 versus 676 (p=NS).

The untreated control animals on the other hand, have significantly decreased positive dP/dt (906 down to 609; p=0.009) and negative dP/dt (850 down to 599; p=0.0332). They also have increased left atrial pressures (14 up to 20; p=0.0169). This again was indicative of the role of myotissue in preventing the decline in left ventricular function that ensues after myocardial infarction.

Morphometric measurement of myocardial infarction size by TTC was done to confirm the effect of cardiomyoplasty on infarct size reduction. As previously described, the infarction size was controlled by positioning the balloon in the mid-left anterior coronary artery (past diagonal branch 1) during each procedure and maintaining inflation for 60 minutes. This, however, was subject to some variability between animals.

Figure 12A:
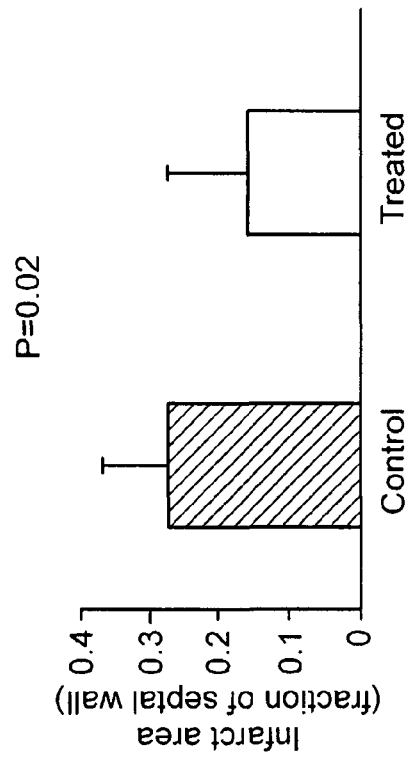
FIGS. 12A and 12B show the improvement in the infarcted region size in treated animals in the interior and septal walls, respectively.
Figure 12B:
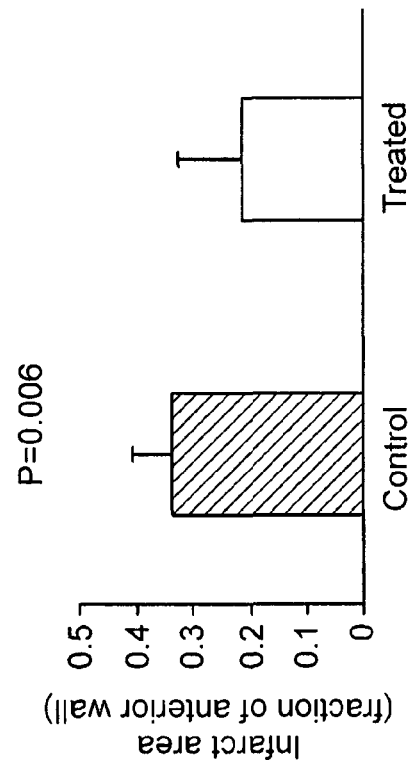

This variability and average infarct size was no different between animal groups at two weeks post-infarction before randomization as measured by echocardiography, e.g., ejection fraction was 50% and 49% in the two groups; p=NS. There was a significant difference in infarct size between untreated controls and animals that received cardiomyoplasty treatment. The percent infarct size in the anterior wall of treated animals was significantly smaller than in the control animals (21.4%±3.3% versus 33.4%±2.2%; p=0.006) as shown in FIG. 12A. Unlike in the acute myocardial infarction model, there was also a significant difference in the infarct size in the untreated septum (16.2%±3.3% and 27.1%±3%; p-value=0.024) as shown in FIG. 12B, indicating a global effect of myotissue on myocardial regeneration.

TTC staining assessment was consistent between two independent observers (corr. coeff=0.82; p=0.0005).

Histological analysis by H&E (hematoxylin-easin) and trichrome staining confirmed the presence of extensive areas of infarction and fibrosis in the anteroseptal area. In the treated animals viable implants could be seen present in multiple tissue sections.

Adjacent to the implants and within the infarct region markedly increased numbers of primitive stem cells positive for mdr-1 were seen. These cells were not as numerous in the untreated control animals (9+6.2 vs. 17+3.9 mean number of cells per 10× power field; p=0.038). Numbers of sca-1 cells were not significantly different between the two groups (13+13 vs. 16+25; p=0.84). C-kiH stem cells on the other hand were more numerous in the control (untreated) animals (7.8+6 vs. 0.6+1.3; p=0.034).

Figure 13:
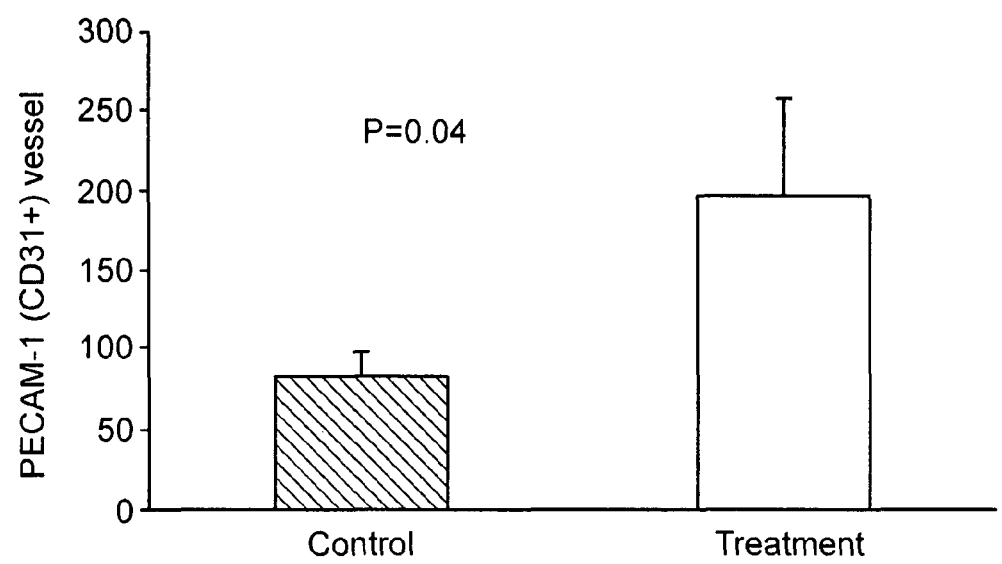
FIG. 13 illustrates the three-fold increase in the number of vessels in treated subjects.

Accordingly, it can be inferred from this result that mdr-1 positive and possibly sca-1 positive adult cardiac stem cells were potentially originating and migrating into the infarct region from the implants. This is in contrast to the trafficking of cardiac progenitors from the bone marrow after infarction, which may be responsible for increased number of c-kiH progenitor cells in the untreated animals. PECAM-1 staining indicated an increase in the number of capillaries and new-vessels in treated animals (FIG. 13).

Figure 14A:
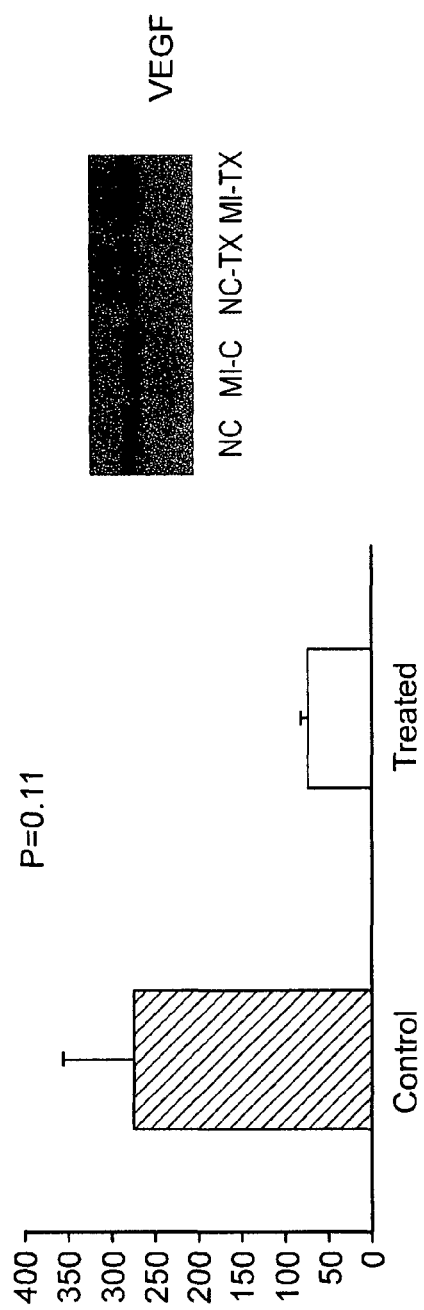
FIGS. 14A and 14B show the levels of angiogenic factors in VEGF and GDF-2, respectively.

In order to explore whether the improvement in myocardial function due to cardiomyoplasty is mediated by neo-angiogenesis, protein expression analysis of infarcted myocardium was performed. Levels of VEGF-2 (23 kDa) protein tended to be two-fold lower in the treated animal group (FIG. 14A). The treatment with autologous cardiomyocytes indicates that there was decreased need for endogenous angiogenesis and increased tissue perfusion as well as tissue repair within the infarct zone.

Figure 14B:
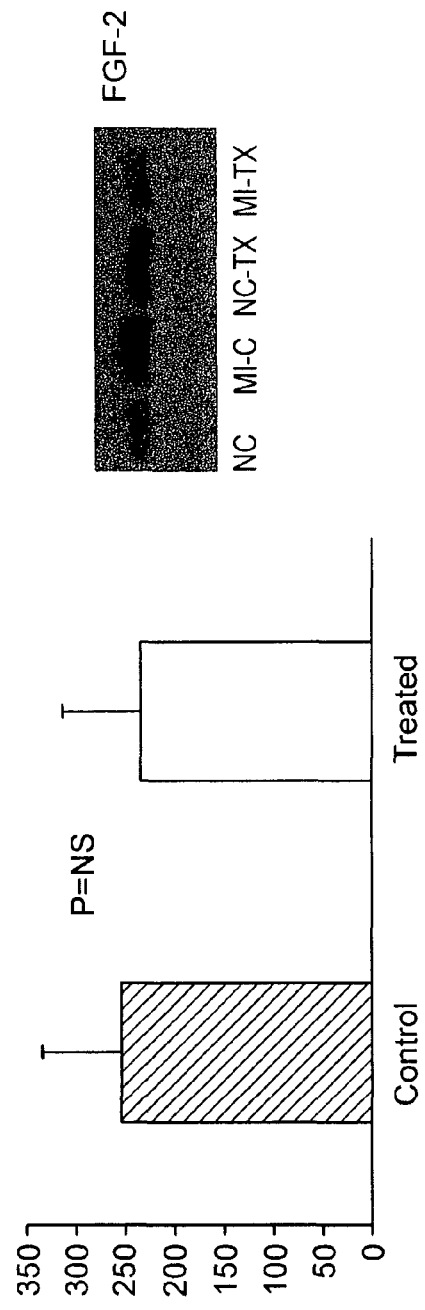

FGF-2 levels, on the other hand, tended to be equally elevated 3-4 fold above baseline in both groups (FIG. 14B).

Figure 15A:
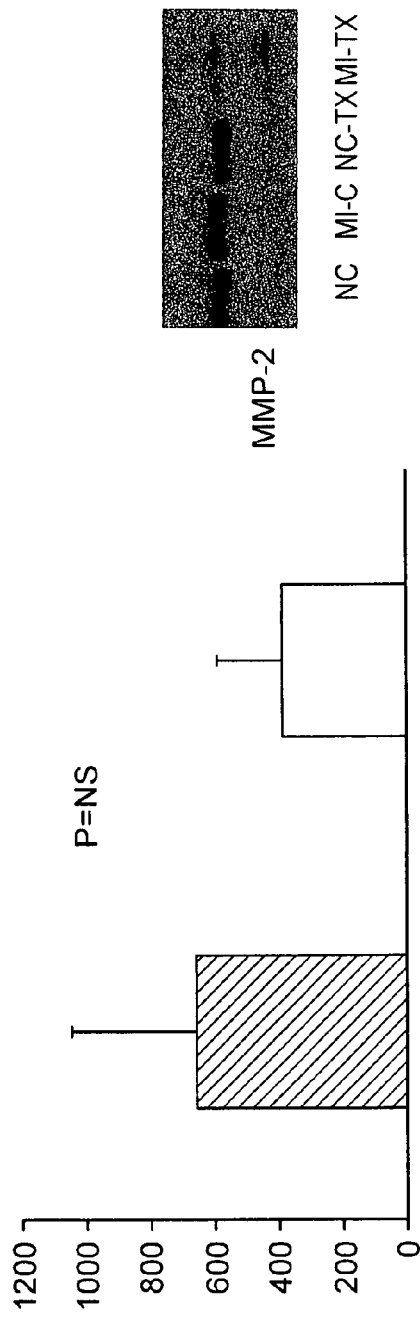
FIGS. 15A and 15B show the matrix metalloproteinase expression for MMP-2 and TIMP-2, respectively.
Figure 15B:
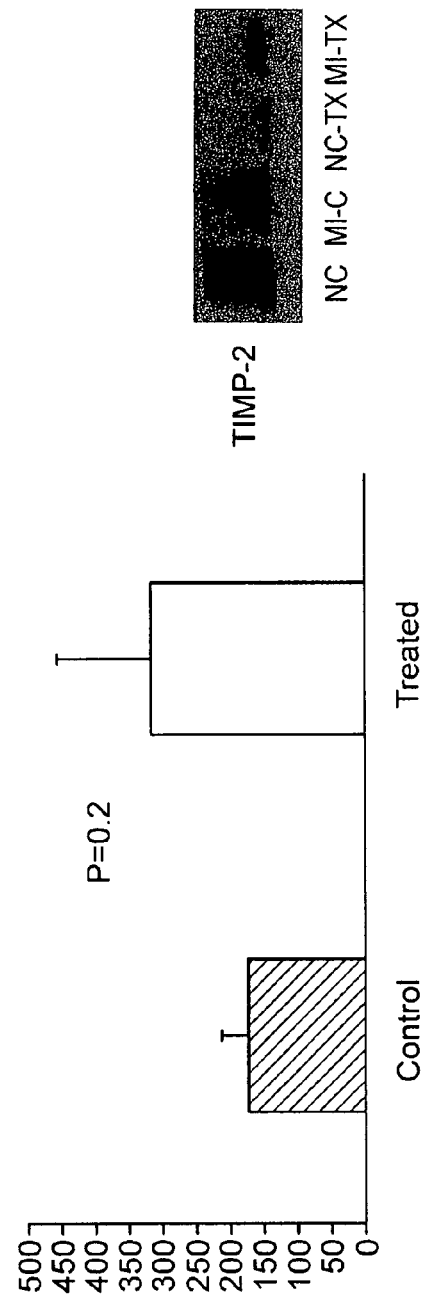

Given the observed effect of myotissue on preventing myocardial dysfunction and left ventricular dilation, the expression of matrix metalloproteinases MMP-2 and -9 was evaluated, as well as tissue inhibitor of matrix metalloproteinase-2 (TIMP-2) that are known to be involved in unfavorable remodeling post-infarction. Preserved myocardial function in treated animals correlated with a trend to two-fold lower levels of MMP-2 (FIG. 15A) and two-fold higher levels of TIMP-2 (FIG. 15B). MMP-9 levels were down-regulated in both animal groups as would be expected from the kinetics of MMP-9 post myocardial infarction.

The embodied methods, which obviate the need for cell culture with its potential complications of infection and decreased cell survival, can be implemented during planned revascularization procedure such as coronary artery bypass grafting (CABG), or via video assisted thoracoscopy for patients who are not candidates for revascularization. These results demonstrate that implantation of myotissue prevents inexorable decline in myocardial function observed after extensive anterior myocardial infarction. This was evident in preservation of ejection fraction, as well as hemodynamic parameters in the treated animals. This is in keeping with the results of prior results in which ejection fraction increased by about 3-7% in acute myocardial infarction setting.

Figure 16:
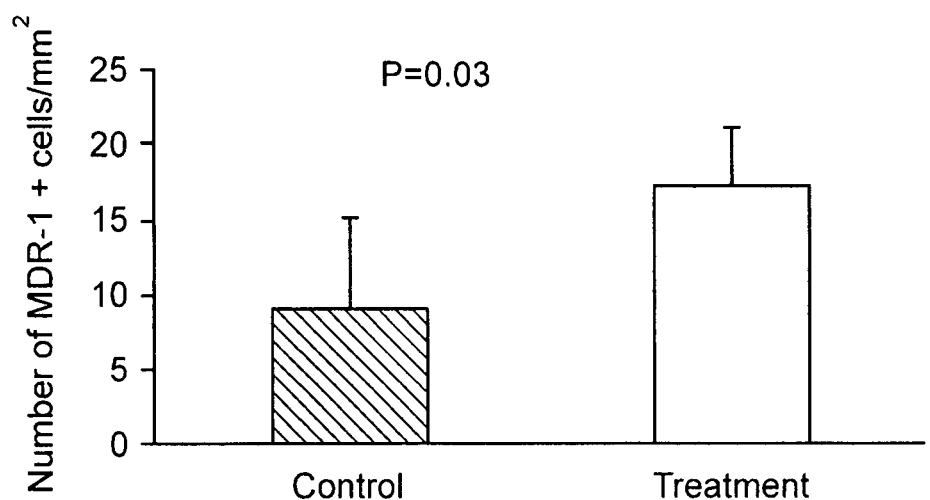
FIG. 16 shows the mdr-1 increase for treated animals.

Cardiomyoplasty in chronic ischemia was shown to decrease infarct size and contractility by SPECT and MRI imaging, respectively, in female mice post-myocardial infarction and were shown to form new vessels. This mechanism is at work given the overall increased number of mdr-l positive stem cells in the infarct zone of treated animals surrounding the implant sites (FIG. 16). Mdr-l positive cells have been shown to differentiate into myocytes, endothelial cells, smooth muscle cells and fibroblasts.

Sca-l is expressed on endothelial cells in addition to stem cells. The present numbers of sca-l positive cells were equivalent between the groups, possibly because of endothelial-staining confounding the true number of sca-l positive stem cells.

Figure 17:
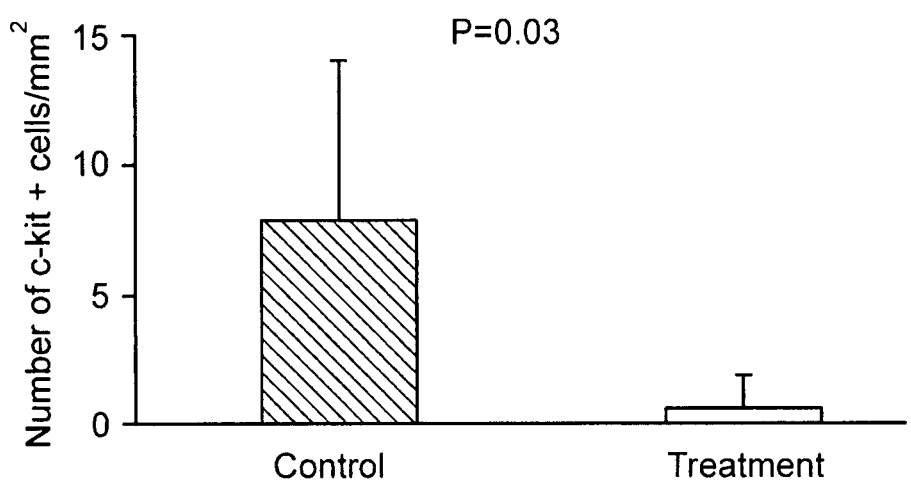
FIG. 17 shows the decrease in c-kit positive for treated animals.
Figure 18:
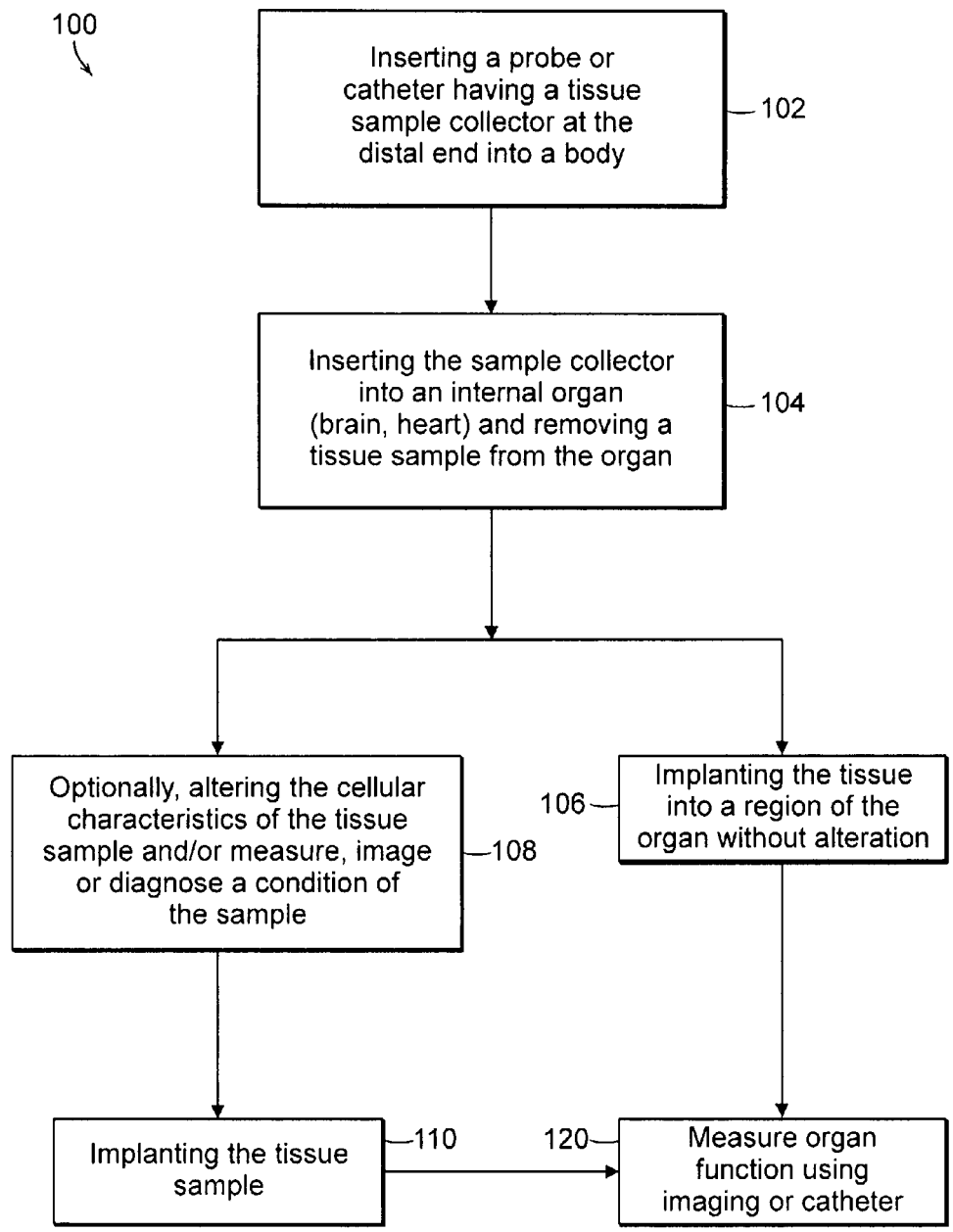
FIG. 18 illustrates a method for removal and implant of a portion of an organ in accordance with a preferred embodiment of the invention.

C-kit positive cells can regenerate multiple lineages and may be more pleuripotent than mdr-l and sca-l positive cells. An increase in c-kit positive cells was found in untreated samples (FIG. 17). Less mature c-kit positive stem cells are in this case derived from bone marrow and recruited in higher numbers to the infarct area given the absence of implant-derived mdr-l and sca-1 cardiomyocyte progenitors.

In adult murine myocardium, sca-l positive c-kit negative cells express cardiogenic transcription factors but not the structural genes making them candidates for cardiac progenitor cells. Indeed, sca-l positive c-kit negative cells home to the infarct-border zone and make up as many as 15% of the myocyte population in this region.

In hypertrophied hearts the numbers of c-kit, mdr-l, and sca-1 positive cells are also increased compared to controls. The numbers of these cells are not equal, however, with c-kit cells outnumbering sca-l and mdr-l cells in this order, suggesting that cardiac progenitors may express these markers at different stages of differentiation. It is possible that mdr-l positive cells are more differentiated than c-kit positive cells and, therefore, owing to the enriched environment of the implants, have a greater survival and differentiation rate in the treated animals.

There is an alternative explanation for this enrichment in mdr-l positive cells in the treated animals. Rather than migrating directly from the implant into the infarct and peri-infarct zones, they may have been recruited from atria and right ventricular outflow tracts of the heart in response to the homing signals provided by the implant tissue.

Isl-l cells, which are the post-natal cardioblasts, are most prevalent in these regions of the heart and may be recruited during myocardial infarction.

The differentiation potential of the adult cardiac stem cells is not only limited by their senescence, i.e., low expression of telomerase reverse transcriptase, but also likely by the trophic factor impoverished milieu of the infarct. In the past this problem was circumvented partly by implanting the myoblasts into peri-infarct hybernating zones using NOGA catheter electromechanical mapping guidance. However, by implanting stem cells together with adjacent intact differentiated cardiomyocytes, the stem cells with those trophic factors necessary for differentiation were provided.

Although stem cells are purportedly more durable than other cells, they also survive poorly in an infarcted and non-perfused environment. Thus, pro-angiogenic microenvironment created by the implants may have been another instrumental factor in increasing the number of viable mdr-l positive cells.

Consistent with these measurements in acute myocardial infarction model, VEGF-2 levels were lower in treated animals at four (4) weeks after the initial myocardial infarction and two weeks after cardiomyoplasty treatment. Note that at four (4) weeks, post-myocardial infarction, when the ejection fraction and other parameters of myocardial function had recovered in animals treated with cardiomyoplasty, VEGF-2 levels can already down-regulated. Animals that were not treated and continue to have lower myocardial perfusion and myocardial dysfunction, still maintain elevated VEGF-2 levels.

In another embodiment of a method 100 in accordance with the invention, a sample can be taken from an animal or human brain and implanted into damaged or diseased tissue to provide cellular regeneration. The probe or catheter is first inserted 102 into the body, a sample collector is inserted 104 into the organ and a tissue sample is removed. The collector can either be repositioned for implantation 106 without any alteration of the sample, or alternatively, the sample can be measured 108 or its cellular characteristics altered prior to implantation 110. The organ function can then be evaluated 120 or monitored.

One embodiment according to the invention is an open chest surgical procedure for autologous myocardial tissue transplantation. A patient with recent myocardial infarction who has open chest surgery for coronary artery bypass graft (CABG) can have myocardial tissue transplantation performed in the same procedure. The patient undergoes median sternotomy in the usual fashion and is placed on by-pass. The heart is fully exposed, which allows for easy access to all the walls of the heart. After sewing on all the necessary bypass grafts (e.g., left internal mammary artery (LIMA) and saphenous vein grafts) to the viable myocardial territories, the territory of the non-viable scar as determined by pre-operative thalium nuclear study or cardiac magnetic resonance delayed enhancement imaging, is treated by autologous myocardial tissue transplantation.

The right ventricular free wall is incised with a number 11 blade. A purse string suture is placed, and a 6 French femoral artery sheath (cut to 5 cm in length) is inserted into the right ventricle. The suture secures the sheath in place and allows for easy repair of the incision at the end of the procedure. Through the sheath side arm, angiographic contrast will be injected to delineate the position of the basal septum. A rigid myocardial transplantation catheter device is inserted through the 6 French sheath and positioned against the basal septum under fluoroscopic or transesophageal echocardiogram guidance. A myocardial tissue graft is obtained by insertion of the sharp distal end of the hypotube completely through the septum and withdrawal of the hypotube. The device is removed from the right ventricle and placed against the myocardial scar (e.g., anterior left ventricular wall, in the case of an anterior myocardial infarction). The sharp edge is positioned perpendicular (optionally at an angle up to 45 degrees) to the myocardial wall and inserted into the wall to the depth determined by the stylet. The stylet is held in place while the sliding mechanism allows for the hypotube to be withdrawn, leaving the biopsy implanted within the left ventricular wall. The catheter device is then moved away from the front wall.

The hypotube is advanced forward to expose the cutting edge at the distal end and the catheter device is reinserted into the right ventricle through the sheath. The process of myocardial graft removal and transplantation is then repeated 6-10 times, depending on the size of the infarct area.

A myocardial tissue transplantation method in accordance with the invention can be performed by open-chest techniques (i.e., thoracotomy), during which the heart is under cardioplegic arrest and circulation is maintained by cardiopulmonary bypass. However, the necessity of stopping the heart significantly heightens the risks associated with such procedures, including the risk of causing ischemic damage to the heart muscle and of causing stroke or other injury due to circulatory emboli resulting from aortic clamping and vascular cannulation. In addition, gross thoracotomy produces significant morbidity and mortality and lengthens recovery. Therefore, in some embodiments, a myocardial tissue transplantation according to the invention is performed using thoracoscopic access into the interior of the heart while the heart is beating.

In the thoracoscopic approach, the ribs and sternum remain intact and are not significantly retracted during the procedure. A working space is created in the patient's chest cavity by collapsing one of the patient's lungs or using jet ventilation techniques. A viewing scope such as an endoscope or endoscopic surgical microscope is then introduced through an intercostal space into the working space to view the exterior of the heart while the penetration is formed and the access device is introduced. The viewing scope may include a video camera to provide a video image of the heart for display on a monitor which can be viewed during the procedure. Alternatively, the heart may be viewed directly through a lens on the viewing scope or through a trocar sleeve positioned in an intercostal space. Access into the chest cavity is obtained through small percutaneous incisions or punctures in the intercostal spaces between the ribs. Trocar sleeves, ports, or other types of percutaneous access cannulae may be placed in these incisions or punctures to protect and retract surrounding tissue to facilitate introduction of instruments into the chest cavity. Small incisions and/or access ports can be placed, for example, in the third, fourth, fifth, or sixth intercostal spaces on a lateral side of the chest. At least three such ports are usually required, one for introduction of the transplantation catheter device, one for introduction of a visualization device such as an endoscope, and one for introduction of other instruments for suturing, retraction, and other purposes. Alternatively, the transplantation tube or catheter device can be inserted through the biopsy channel of an endoscope or can include a fiber optic cable for visualization.

The patient is prepared for cardiac surgery in the conventional manner, and general anesthesia is induced. The patient is positioned on the patient's left side so that the right lateral side of the chest is disposed upward. Two to three small incisions 2-3 cm in length are made between the ribs, usually in the third, fourth, or fifth intercostal spaces. Thoracoscopic access ports (e.g. trocar sleeves or other tubular cannulae), are positioned in each incision to retract away adjacent tissue and protect it from trauma as instruments are introduced into the chest cavity. Access ports have an outer diameter which does not require retraction, cutting or removal of ribs, preferably less than 14 mm, and an axial passage with a diameter less than about 12 mm. Access ports may also be non-circular in cross-section, or may be made of a flexible material to deform into a non-circular shape when introduced between two ribs. The right lung is deflated using conventional techniques, usually by introducing a tube through the patient's trachea into the right lung and applying a vacuum through the tube to deflate the lung. An endoscopic visualization device such as a thoracoscope connected to a video monitor is introduced through one of access ports to visualize the interior of the chest cavity.

Visualization within the interior of the heart may be provided by an ultrasonic probe positioned in the patient's esophagus, on the surface of the patient's chest, or in the chest cavity adjacent or in contact with the exterior of the heart to ultrasonically image the interior of the heart. Alternatively, an endoscope with a translucent bulb or balloon over its distal end may be introduced into the heart through the access device or through a separate incision in the wall of the heart to allow video-based or direct visualization of the interior of the heart. An angioscope introduced into the heart endovascularly through a peripheral vessel may also be used for intracardiac visualization. Fluoroscopy is an additional technique for visualization.

A purse string suture is then placed in the wall of heart around the site at which it is desired to introduce the access device. This is accomplished by using thoracoscopic needle drivers to introduce into the chest cavity a curved suture needle attached to one end of a suture thread, and to drive the needle through the heart wall to form a running stitch in a circular pattern approximately 12-14 mm in diameter. A double-armed suture may also be used, wherein the suture thread 110 has needles at both ends, allowing each needle to be used to form one semi-circular portion of the purse-string. Suture thread may be long enough to allow both ends of the suture to be drawn outside of the chest cavity once purse-string suture has been placed, or it may be shorter and manipulated within the chest cavity using thoracoscopic instruments. Suture needle is then cut from thread using thoracoscopic scissors.

A tubular access device with a length of about 10 cm and an inner diameter of about 5 mm is then introduced through the area surrounded by the purse string suture. The access device may include means for sealing peripherally around the area of penetration in the muscular heart wall. The sealing means can include one or a pair of inflatable balloons, a radially-expandable portion of the tubular body, or a flange at the distal end of the body. The access device may further include an obturator positionable within an inner lumen of the tubular access device. The obturator has means, such as a blade, at its distal end for penetrating the muscular wall of the heart. The access device may include a hemostasis valve in the inner lumen to prevent blood flow out of the heart through the inner lumen, and to allow instruments to be introduced through the inner lumen while maintaining hemostasis in the inner lumen.

Once the septal biopsies have been retrieved and transplanted to the infarction zone, the access device is withdrawn from the penetration in the wall of the heart. If a balloon or a radially expanding portion of the access device has been utilized for hemostasis, it is first deflated or radially contracted. As the distal end of the access device is withdrawn, the purse string suture in the heart wall surrounding the access device is pulled tight, closing the penetration. Knots are then formed in the purse string suture, either intracorporeally using endoscopic instruments, or extracorporeally, after which the knots are pushed into the body cavity and against the heart wall using an endoscopic knot pusher. Alternatively, the penetration in the heart wall may be closed using endoscopic suturing or stapling techniques after the access device has been withdrawn. All access ports are then withdrawn, percutaneous incisions and punctures are closed, and the patient is recovered from anesthesia.

The neck is prepped and the right internal jugular vein is cannulated percutaneously with a needle in the same fashion as is done for central line insertion. A 6 French sheath is placed in the internal jugular vein over the wire. This sheath is used for insertion of a balloon-tip Swan-Ganz catheter from IJ, via the superior vena cava and right atrium into the right ventricle. This is then exchanged for a 55 cm multipurpose guiding catheter. A myocardial tissue transplantation catheter device with a rigid hypotube length of 55 cm is then placed in the multipurpose guide to protect the structures from the sharp edges of the device. The guide allows for positioning of the device with the right ventricle up against the septum under fluoroscopic guidance with care taken not to injure the pulmonary outflow tract. After the myocardial tissue graft is obtained and protected inside the hypotube, the transplantation catheter device is taken out through the guide catheter and the sheath and inserted via the 5 mm port. Under direct visualization of the thoracoport camera, the wall of the left ventricle to be implanted can be adequately exposed. The beating heart can be stabilized with a grasper. The procedure is repeated until 6-10 grafts have been transplanted. The port sites are closed in two layers of sutures, and the patient is extubated.

Yet another embodiment in accordance with the invention is an intravascular procedure for autologous myocardial tissue transplantation. A percutaneous intravascular procedure is preferred in patients who are candidates for concomitant percutaneous revascularization or have prohibitively high operative risk for open chest surgery. This catheter-based approach is not suitable for patients with severe aortic stenosis and aortic valve calcification.

The patient undergoes femoral artery cannulation in a standard fashion with a 6 Fr sheath. A standard 0.035" guide wire is advanced into the aorta, and a pigtail catheter is used to initially enter the left ventricle in an atraumatic fashion. The pigtail catheter is then exchanged for a hockey stick guide catheter, or alternatively with a transplantation catheter device having a sheath with a deflectable tip. The guide catheter (or the deflectable sheath) is then positioned against the basal septum with fluoroscopic guidance and EKG monitoring for LBBB injury. A 90 cm transplantation catheter device is then advanced though the guide catheter to obtain a myocardial biopsy from the ventricular septum. The transplantation catheter device is then retracted into the guiding catheter, and the guiding catheter is positioned against the treatment area (infarcted area of the left ventricle). The transplantation catheter device is advanced forward for implantation into the ventricular wall. The hypotube is pulled back over the stationary stylet leaving the implant behind in the infarcted area. The transplantation catheter is then retracted into the guiding catheter. The process of biopsy retrieval and implantation is repeated 6-10 times.

In some embodiments the myocardial biopsy is decellularized, leaving an extracellular scaffold which is implanted in the infarcted area. Various methods can be used, including treating the harvested tissue with alkaline or acid, detergents, and enzymes. For such embodiments, the biopsy specimens are collected by aspiration into a container. From the container, they can be collected and transferred to a solution containing a cell disrupting agent. By way of example, the tissue specimens can be placed into a 50 mL conical tube and submerged in 1.0M NaOH for 60 minutes. Afterwards they are washed with deionized water twice for 15 minutes each. The tissues are then immersed in 5% propylene oxide solution in 0.2M carbonate buffer and incubated with shaking at room temperature for 72 hours. The tissues are then washed twice with deionized water twice for 20 minutes each, and then dried in an oven at 70° C. for 48 hours. The absence of visible nuclei after H&E staining can be used to confirm the decellularization process. A decellularized tissue scaffold of this type can be implanted into a myocardial infarction area as is, or it can be recellularized prior to implantation. For recellularization, the scaffold is seeded with cells from the patient (e.g., cardiomyocytes, fibroblasts, myoblasts, stem cells, progenitor cells, or mixtures thereof) by adding the scaffold to a suspension of the desired cells in culture medium and placing the suspension into a bioreactor or an incubator for a period of several hours to several days, so as to allow the cells to partially or completely repopulate the scaffold.

Still another embodiment is an autologous brain tissue transplantation procedure. Transplantation catheter devices for collecting and implanting a brain biopsy are similar to the scaffold loading devices described above. The brain tissue collection catheter device employs gentle aspiration of the brain biopsy specimen and its collection in a container attached to the device, and optionally incorporated into the device handle. The inner diameter of the distal tip of the catheter is 150 microns, which limits damage to the donor site. Once harvested, the tissue specimen, suspended in sterile saline, can be treated, e.g., with growth factors or other agents, or packaged in a polymer scaffold. Subsequent to any treatment and/or packaging, the tissue graft is taken up in the transfer catheter device, which is used to implant it into the target tissue.

A stereotactic frame is placed on the patient's skull. An incision is made in a predetermined position over the frontal lobe of the unaffected hemisphere and another incision is made over the site of the infarction. Burr holes are then drilled at these positions. See Freed et al., N. Engl. J. Med. 344:710 (2001), incorporated herein by reference, for description of the implantation of cells into the brain by this route. The rigid brain tissue collection catheter device is inserted through the burr hole at the donor area. The collection catheter utilizes a double bore tube, with one channel for aspiration of the tissue graft and the second channel for supplying a stream of sterile saline to the donor area, which allows the tissue graft to be swept up into the aspiration channel in a stream of fluid. A side port on the device is attached to a vacuum device which applies a gentle, regulated negative pressure within the aspiration channel of the catheter for aspiration of the tissue, which is collected in a specimen chamber together with aspirated fluid from the donor area. The patient is awake throughout the procedure and under EEG monitoring to assess their neurologic status.

After collection, the tissue graft is placed into a 37° C. incubator. The graft is prepared for implantation by wrapping it in a polymer gel containing poly(lactic-co-glycolic acid) (PLGA)/poly(L-lactic acid) (PLLA) polymer with the aid of a stereomicroscope and micromanipulators. See Tomita et al., Stem Cells 23:1570 (2005), incorporated herein by reference, for a description of the production and use of PLLA/PLGA polymer substrates. Alternatively, the graft is deposited onto a PLLA/PLGA polymer layer in a culture dish and incubated in culture for at least several hours prior to insertion into the infarcted area. The jacketed graft is then taken up into a delivery catheter. The delivery catheter is similar to the myocardial transplantation catheter used for open chest surgery applications. It has a rigid hypotube containing a retractable stylet, but is shorter than the heart catheter, having a hypotube of 5 cm in length. The inner diameter of the hypotube should be greater than that of the tissue collection catheter to allow for the additional volume of the polymer scaffold jacket; in this case the internal diameter of the hypotube in the transfer catheter is 300 μm. The transfer catheter containing the graft is placed into the burr hole over the infarction site. The brain implant is then gently flushed into the infarct zone by advancing the stylet through the hypotube lumen. Finally the transfer catheter device is removed from the burr hole at the infarction site, and the incisions at donor and receptor sites are closed.

Another embodiment in accordance with the invention is an intravascular procedure for autologous brain tissue transplantation. In this variation of the procedure presented above, access to the donor brain tissue is obtained via the venous sinus structures of the brain. Internal jugular access is obtained on the side contralateral to the stroke. A 5 French catheter is advanced to the venous sagittal sinus overlying the frontal lobes. The transplantation catheter device for this procedure includes a flexible double bore tube of 30 cm length. The tube is advanced through the wall of the sagittal sinus into the frontal lobe, and the brain tissue graft is gently aspirated into a specimen chamber by applying vacuum to the aspiration channel and introducing sterile saline into the second channel. The internal jugular vein on the side ipsilateral to the stroke is then cannulated for implantation. A 5 French guide catheter is positioned into a venous structure overlying the infarct region, and the delivery catheter is inserted through the guide catheter. The graft is implanted in the infartion area by advancing the stylet of the delivery catheter.

Still another embodiment is a procedure for autologous transplantation of brain tissue to retina. A brain biopsy is obtained by one of the methods described above. Implantation of the biopsy into the subretinal space is performed under direct observation using a binocular surgical microscope and viewed through a dilated pupil after topical application of tropicamide 1%. For implant placement a conjunctival incision and small sclerotomy is made using an extrafine disposable scalpel. The implant is 150 microns in diameter and is inserted through the sclerotomy into the subretinal space using either fine #5 Dumont forceps (Fine Science Tools, North Vancouver, British Columbia, Canada) or using a brain transplantation delivery catheter as described above. The implant can be visualized through the pupil using standard illumination. At the conclusion of all surgeries, fundus examination is performed via surgical microscope to confirm successful graft placement.

While the invention has been described in connection with specific methods and apparatus, those skilled in the art will recognize other equivalents to the specific embodiments herein. It is to be understood that the description is by way of example and not as a limitation to the scope of the invention and these equivalents are intended to be encompassed by the claims set forth below.

What is claimed is:

1. A device for repairing an injured myocardium by tissue implantation and cellular regrowth, the device comprising:
a flexible catheter body;
a rigid sleeve attached to a distal end of the catheter body, the sleeve having a distal cutting edge extending around a distal opening for insertion into myocardial tissue to remove a tissue sample and retain the tissue sample in a tubular cavity of the sleeve, the tubular cavity having an internal diameter in a range between about 100 micrometers and about 1000 micrometers; and
a moveable element within the tubular cavity of the sleeve, the moveable element being displaced proximally by the tissue sample retained within the tubular cavity, the moveable element being attached to a cable extending through the catheter body, the cable being actuated for axial translation within the catheter body to move the moveable element in a distal direction relative to the sleeve such that the tissue sample can be displaced from the sleeve through the distal opening with the moveable element.

2. The device of claim 1 wherein the sleeve comprises a tube.

3. The device of claim 2 wherein the tube comprises stainless steel or Nitinol.

4. The device of claim 2 wherein the tubular cavity receives a myocardial tissue sample, the sleeve having a length that extends through a septal wall of a mammalian subject.

5. The device of claim 2 wherein the tube is a cutting cannula.

6. The device of claim 1 wherein the distal cutting edge of the sleeve is peripheral about the distal opening.

7. The device of claim 6 wherein the sleeve further comprises a stop element that constrains movement of the moveable element.

8. The device of claim 7 wherein the stop is positioned on an inner wall of the sleeve, the stop having a distal surface positioned in a range of 0.5 to 2.0 centimeter from the distal end of said sleeve.

9. The device of claim 1 wherein the moveable element comprises a stylet that moves in an axial direction within the sleeve.

10. The device of claim 9 wherein the stylet includes a rear stopping portion and a front portion such that a stop element within the sleeve and the rear stopping portion limit movement of the front portion.

11. The device of claim 9 wherein the stylet has one or more apertures to allow fluid flow between proximal and distal sides of the stylet.

12. The device of claim 1 wherein the catheter body has a length to extend percutaneously into a human heart.

13. The device of claim 12 wherein the sleeve has a circular distal opening.

14. The device of claim 13 wherein the catheter body has a length of at least 45 cm.

15. The device of claim 13 wherein the catheter body has a flexible portion with a length of at least 80 cm.

16. The device of claim 12 wherein the catheter body is attached to a handle at a proximal end.

17. The device of claim 16 wherein the handle comprises an actuator that is connected to the moveable element.

18. The device of claim 17 wherein the actuator is connected to the moveable element with the cable.

19. The device of claim 16 wherein the handle comprises a second actuator that moves a distal end of the catheter in a radial direction.

20. The device of claim 16 wherein the handle comprises a third actuator that actuates movement of a stop within the sleeve that constrains movement of the moveable element.

21. The device of claim 12 wherein the catheter body further comprises a flexible tube having a length in a range of 30 cm to 100 cm.

22. The device of claim 12 wherein the catheter body has an outer diameter sized to slide within a guide catheter.

23. The device of claim 22 wherein the guide catheter has a distal end rigidly positioned at an oblique angle relative to a longitudinal axis of the catheter body.

24. The device of claim 23 wherein the guide catheter slides over a guidewire.

25. The device of claim 12 wherein the catheter body comprises at least three tubular bodies concentrically positioned.

26. The device of claim 1 wherein the tubular cavity has a distal opening and a length in a range of 5 mm to 15 mm.

27. The device of claim 1 wherein the tubular cavity is in fluid communication with a suction device.

28. The device of claim 1 wherein the tubular cavity is in fluid communication with a fluid source.

29. The device of claim 1 wherein the catheter body has a length of at least 20 cm that is attached to a handle.

30. The device of claim 1 wherein the sleeve is detachable from a handle to provide a disposable device.

31. The device of claim 1 further comprising a system for processing a tissue sample.

32. The device of claim 1 further comprising a pull wire to orient the sleeve at the distal end of a catheter body at an oblique angle.

33. The device of claim 1 further comprising a monitor to observe patient condition.

34. The device of claim 1 further comprising a pressure sensor to monitor fluid pressure in the sleeve.

35. The device of claim 1 wherein the sleeve comprises a metal tube having a length of 1 cm to 10 cm.

36. The device of claim 1 wherein the sleeve is manually extended relative to a guide tube.

37. A device for repairing tissue by tissue implantation and cellular regrowth, the device comprising:
 a flexible probe having a rigid sleeve at a distal end of a tubular body, the sleeve having a cutting edge extending around a distal opening and a tubular cavity within the sleeve, the tubular cavity having an internal diameter in a range between about 100 micrometers and about 1000 micrometers such that a tissue sample can be received into the tubular cavity through the distal opening;
 a control handle at the proximal end of the probe, the handle having a first actuator and a second actuator to control an adjustable angular position of the distal end of the probe relative to a tissue region; and
 a moveable element within sleeve, the moveable element being attached to a cable extending from the handle through the tubular body such that the first actuator operates to translate the moveable element within the sleeve at the distal end of the tubular body, the moveable element having a distal surface that is displaced proximally by the tissue sample received within the tubular cavity, wherein distal movement of the moveable element displaces the tissue sample through the distal opening of the sleeve for implantation in the tissue region.

38. The device of claim 37 wherein the sleeve penetrates myocardial tissue to cut a myocardial tissue sample from a heart surface.

39. The device of claim 37 wherein the sleeve comprises a metal tube mounted at a distal end of a flexible tube.

40. The device of claim 37 further comprising a stop element within the sleeve, the stop element limiting longitudinal movement of the moveable element in a proximal direction within the sleeve.

41. The device of claim 37 wherein the probe has a length of at least 20 cm such that the sleeve can be inserted through a guide tube into myocardial tissue.

42. The device of claim 37 further comprising a suction device attached to a tube of the probe.

43. The device of claim 37 wherein the probe comprises a flexible tubular body connected to the handle and the sleeve.

44. The device of claim 37 wherein the cutting edge extends around a peripheral edge of a metal tube.

* * * * *